(12) United States Patent
Vaino et al.

(10) Patent No.: US 10,407,447 B2
(45) Date of Patent: *Sep. 10, 2019

(54) PANTOTHENATE DERIVATIVES FOR THE TREATMENT OF NEUROLOGICAL DISORDERS

(71) Applicant: Retrophin, Inc., San Diego, CA (US)

(72) Inventors: Andrew Vaino, San Diego, CA (US); Marek Biestek, San Diego, CA (US); Martin Shkreli, San Diego, CA (US)

(73) Assignee: Retrophin, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/863,683

(22) Filed: Jan. 5, 2018

(65) Prior Publication Data

US 2018/0291045 A1 Oct. 11, 2018

Related U.S. Application Data

(63) Continuation of application No. 15/031,691, filed as application No. PCT/US2014/062451 on Oct. 27, 2014, now Pat. No. 9,896,464.

(60) Provisional application No. 61/895,498, filed on Oct. 25, 2013.

(51) Int. Cl.
  *C07F 9/24* (2006.01)
  *C07F 9/572* (2006.01)
  *C07F 9/6561* (2006.01)

(52) U.S. Cl.
  CPC ............ *C07F 9/2458* (2013.01); *C07F 9/242* (2013.01); *C07F 9/2408* (2013.01); *C07F 9/5728* (2013.01); *C07F 9/65616* (2013.01)

(58) Field of Classification Search
  None
  See application file for complete search history.

(56) References Cited

U.S. PATENT DOCUMENTS 9,896,464 B2 * 2/2018 Vaino

FOREIGN PATENT DOCUMENTS

| AU | 2013251345 B2 | 8/2017 |
| CN | 104520307 B | 12/2016 |
| JP | 2009-504704 A | 2/2009 |
| RU | 2002110463 A | 2/2004 |
| WO | 01/21772 A2 | 3/2001 |
| WO | 03/008626 A2 | 1/2003 |
| WO | 2007/020193 A2 | 2/2007 |

OTHER PUBLICATIONS

Hanna et al., Medscape, "Pantothenate Kinase-Associated Neurodegeneration (PKAN), published on line at emedicine.medscape.com/article/1150519-overview", 8 pages; updated Dec. 7, 2016.*

Balibar et al., "Pantethine Rescues Phosphopantothenoylcysteine Synthetase and Phosphopantothenoylcysteine Decarboxylase Deficiency in *Escherichia coli* but not *Pseudomonas aeruginosa*," *Journal of Bacteriology* 193(13). 3304-3312, 2011.

Derudas et al., "The Application of Phosphoramidate Protide Technology to Acyclovir Confers Anti-HIV Inhibition", *J. Med. Chem.* 52:5520-5530, 2009.

Garcia et al., "Germline Deletion of Pantothenate Kinases 1 and 2 Reveals the Key Roles for CoA in Postnatal Metabolism," *PLoS One* 7(7):e40871. doi: 10.1371/journal.pone.0040871, Jul. 2012, 13 pages.

Gregory et al., "Pantothenate Kinase-Associated Neurodegeneration," NCBI Bookshelf, 22 pages, accessed on Jun. 30, 2014.

Hanna et al., "Hallervorden-Spatz Disease" [online], updated on Feb. 28, 2012, URL http://emedicine.medscape.com/article/1150519-overview.

Hayflick, "Unraveling the Hallervorden-Spatz syndrome: pantothenate kinase-associated neurodegeneration is the name . . . " *Curr. Opin. Pediatr.* 15:572-577, 2003.

Hecker et al., "Prodrugs of Phosphates and Phosphonates," *J. Med. Chem.* 51:2328-2345, 2008.

Hwang et al., "Enzymatic and Cellular Study of a Serotonin N-acetyltransferase Phosphopantetheine-based Prodrug," *Bioorganic & Medicinal Chemistry* 15:2147-2155, 2007.

International Search Report, dated Jul. 4, 2013, for International Application No. PCT/US2013/038458, 4 pages.

International Search Report and Written Opinion dated Jan. 29, 2015, in corresponding PCT Application No. PCT/US2014/062451, 11 pages.

Jackowski et al., "Metabolism of 4'-Phosphopantetheine in *Escherichia coli*," *Journal of Bacteriology* 158(1):115-120, 1984.

Madela et al., "Progress in the development of anti-hepatitis C virus nucleoside and nucleotide prodrugs," *Future Med. Chem.* 4(5):625-650, 2012.

(Continued)

*Primary Examiner* — Savitha M Rao
*Assistant Examiner* — Gregg Polansky
(74) *Attorney, Agent, or Firm* — Seed IP Law Group LLP

(57) ABSTRACT

Compounds having the following formula (E):

Formula E

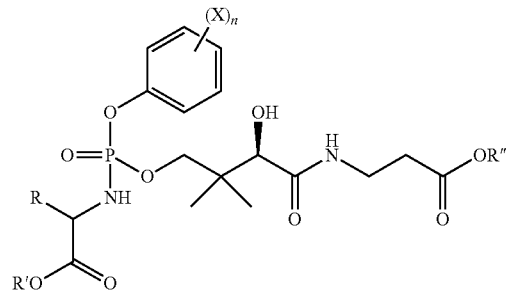

or a pharmaceutically acceptable salt thereof, wherein R, R', R", X and n are as defined herein are provided. Methods comprising use of such compounds for the treatment of neurologic disorders, such as pantothenate kinase-associated neurodegeneration, and pharmaceutical compositions containing such compounds, and their use in treatment of neurologic disorders are also provided.

14 Claims, No Drawings

(56) References Cited

OTHER PUBLICATIONS

McGuigan et al., "Aryl Phosphoramidate Derivatives of d4T Have Improved Anti HIV Efficacy in Tissue Culture and May Act by the Generation of a Novel Intracellular Metabolite," *J. Med. Chem.* 39:1748-1753, 1996.

Pellecchia et al., "The diverse phenotype and genotype of pantothenate kinase-associated neurodegeneration," *Neurology* 64:1810-1812, 2005.

\* cited by examiner

PANTOTHENATE DERIVATIVES FOR THE TREATMENT OF NEUROLOGICAL DISORDERS

BACKGROUND

Technical Field

The present invention relates to pantothenate derivatives for the treatment of neurologic disorders (such as pantothenate kinase-associated neurodegeneration), pharmaceutical compositions containing such compounds, and their use in treatment of neurologic disorders.

Description of the Related Art

Pantothenate kinase-associated neurodegeneration (PKAN) is a form of neurodegeneration with brain iron accumulation (NBIA) that causes extrapyramidal dysfunction (e.g., dystonia, rigidity, choreoathetosis) (A. M. Gregory and S. J. Hayflick, "Neurodegeneration With Brain Iron Accumulation", *Orphanet Encyclopedia*, September 2004). PKAN is thought to be a genetic disorder resulting from lack of the enzyme pantothenate kinase, which is responsible for the conversion of pantothenate (vitamin B-5) to 4'-phosphopantothenate. 4'-Phosphopantothenate is subsequently converted into Coenzyme A (CoA) (as shown below) (R. Leonardi, Y.-M. Zhang, C. O. Rock, and S. Jackowski, "Coenzyme A: Back In Action", *Progress in Lipid Research*, 2005, 44, 125-153).

In particular, pantothenate is converted to 4'-phosphopantothenate via the enzyme pantothenate kinase (PANK), which is converted to 4'-phosphopantothenoylcysteine via the enzyme 4'-phosphopantothenoylcysteine synthase (PPCS), and subsequently decarboxylated to 4'-phosphopantethine via 4'-phosphopantothenoylcysteine decarboxylase (PPCDC). 4'-phosphopantethine is then appended to adenosine by the action of phosphosphpantethine adenyltransferease (PPAT) to afford dephospho CoA, which is finally converted to coenzyme A (CoA) via dephospho-CoA kinase (DPCK).

Classic PKAN usually presents in a child's first ten to fifteen years, though there is also an atypical form that can occur up to age 40. PKAN is a progressively degenerative disease, that leads to loss of musculoskeletal function with a devastating effect on quality of life.

One approach to treating PKAN could be to administer 4'-phosphopantothenate. This approach has been mentioned in the literature, but it has been recognized that the highly charged molecule would not be able to permeate the lipophilic cell membrane (C. J. Balibar, M. F. Hollis-Symynkywicz, and J. Tao, "Pantethine Rescues Phosphopantothenoylcysteine Synthetase And Phosphopantothenoylcysteine Decarboxylase Deficiency In *Escherichia Coli* But Not In *Pseudomonas Aeruginosa*", *J. Bacteriol.*, 2011, 193, 3304-3312).

BRIEF SUMMARY

Embodiments of the present invention relate to particular precursor small molecules of 4'-phosphopantothenate or a

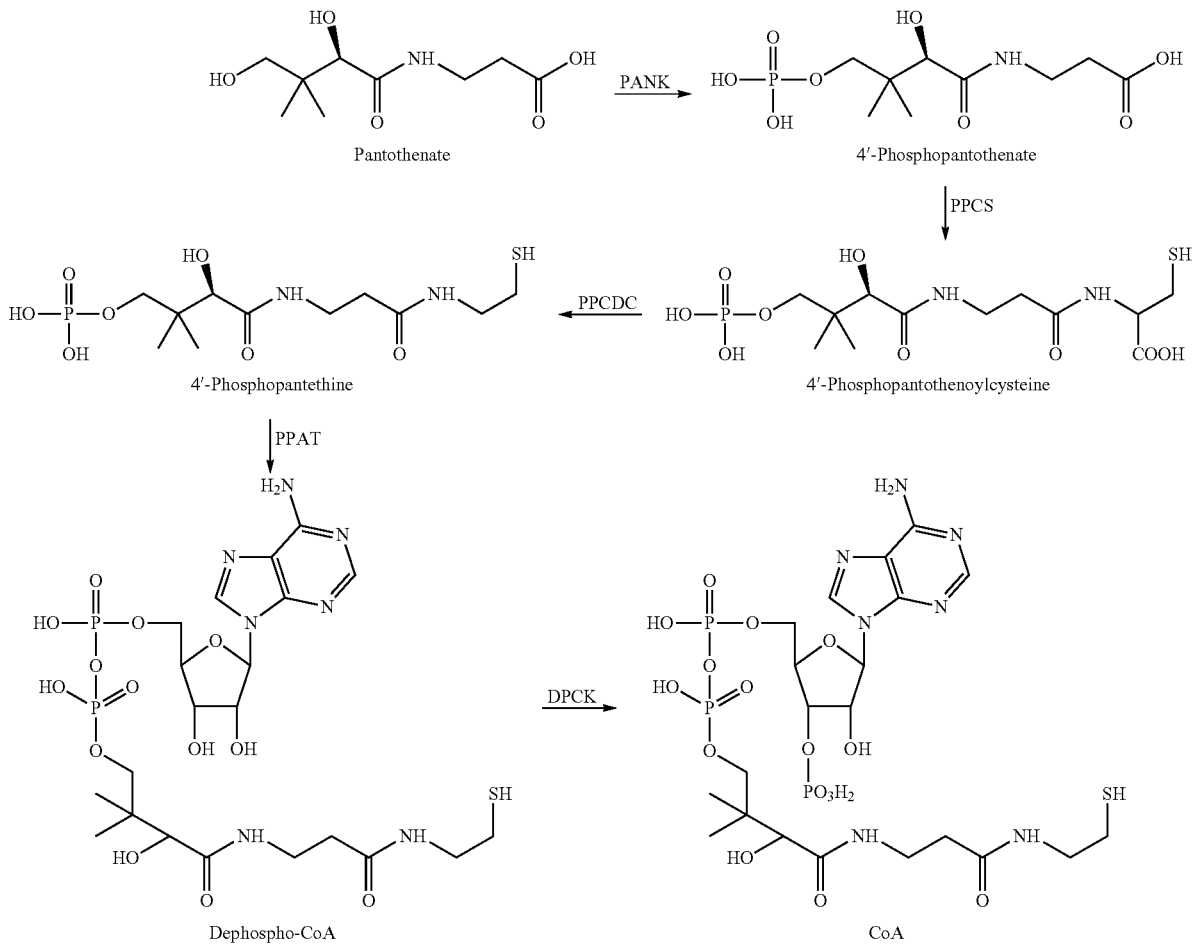

surrogate for 4'-phosphopantothenate. These compounds are expected to have greater cell permeability than 4'-phosphopantothenate. Without wishing to be bound by any particular theory, it is believed that the replacement of 4'-phosphopantothenate, or the use of a surrogate for it, will permit the body to synthesize CoA or an active variant of it. Thus, these compounds may be useful for treating disorders resulting from a deficiency of 4'-phosphopantothenate and/or CoA.

Accordingly, in one embodiment a compound having the following formula (A) is provided:

Formula A

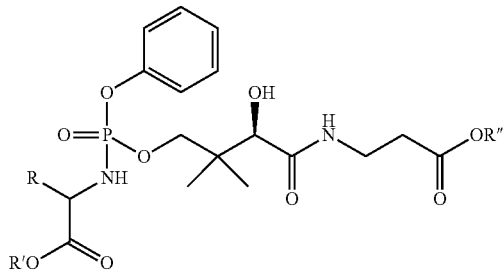

or a pharmaceutically acceptable salt thereof, wherein R, R', and R" are as defined herein.

Still other embodiments provide a compound having the following formula (B):

Formula B

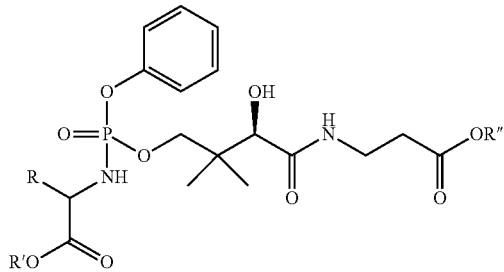

or a pharmaceutically acceptable salt thereof, wherein R is methyl, R' is isopropyl, and R" is methyl, ethyl, isopropyl, neopentyl, or benzyl.

Yet another embodiment provides a compound having the following formula (C):

Formula C

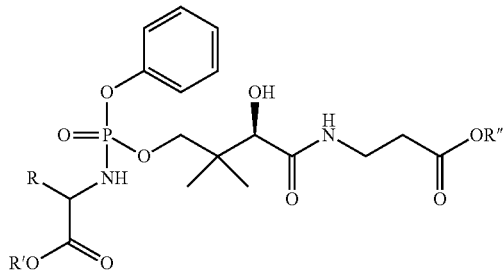

or a pharmaceutically acceptable salt thereof, wherein R is methyl, R' is neopentyl, and R" is methyl, ethyl, isopropyl, neopentyl, or benzyl.

In still other embodiments are directed to a compound having the following formula (D):

Formula D

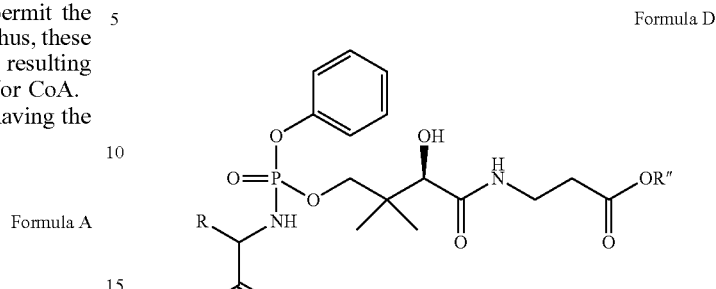

or a pharmaceutically acceptable salt thereof, wherein R, R' and R" are as defined in Table 1 herein.

In another embodiment, a compound having the following formula (E) is provided:

Formula E

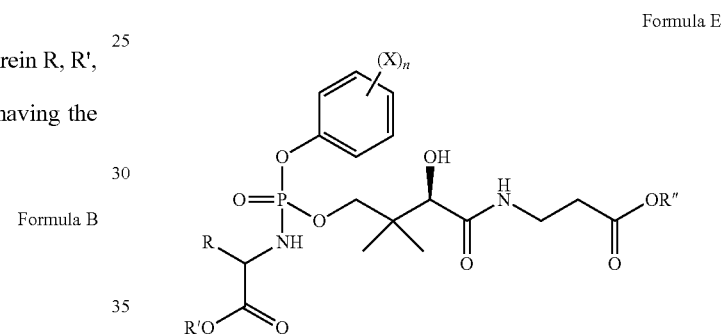

or a pharmaceutically acceptable salt thereof, wherein R, R', R", X, and n are as defined herein.

Pharmaceutical compositions comprising a compound of the present invention, and a pharmaceutically acceptable excipient, as well as methods for use and preparation of the compounds are also provided in various embodiments.

These and other aspects of the invention will be apparent upon reference to the following detailed description.

DETAILED DESCRIPTION

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Unless defined otherwise, all technical and scientific terms used herein have the same meaning as is commonly understood by one of skill in the art to which this invention belongs. As used in the specification and claims, the singular form "a", "an" and "the" include plural references unless the context clearly dictates otherwise.

As used herein, certain items may have the following defined meanings.

As used in the specification and claims, the singular for "a", "an", and "the" include plural references unless the context clearly dictates otherwise. For example, the term "a cell" includes a plurality of cells, including mixtures thereof. Similarly, use of "a compound" for treatment of preparation of medicaments as described herein contemplates using one or more compounds of the invention for such treatment or preparation unless the context clearly dictates otherwise.

As used herein, the term "comprising" is intended to mean that the compositions and methods include the recited elements, but not excluding others. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the composition of this invention. Embodiments defined by each of the transitional terms are within the scope of this invention.

The term "alkyl" refers to a straight or branched hydrocarbon chain radical consisting solely of carbon and hydrogen atoms, containing no unsaturation. Unless otherwise specified, the term "alkyl" refers to a group having from one to eight carbon atoms (for example, one to six carbon atoms (i.e., $C_1$-$C_6$), or one to four carbon atoms (i.e., $C_1$-$C_4$)), and which is attached to the rest of the molecule by a single bond. Examples of alkyl groups include, but are not limited to, methyl, ethyl, n-propyl, i-propyl, n-butyl, t-butyl, s-butyl, n-pentyl, neopentyl and s-pentyl.

The term "alkenyl" refers to an aliphatic hydrocarbon group containing a carbon-carbon double bond and which may be a straight or branched chain. Unless otherwise specified, the term "alkenyl" refers to a group having 2 to about 10 carbon atoms, e.g., ethenyl, 1-propenyl, 2-propenyl (allyl), iso-propenyl, 2-methyl-1-propenyl, 1-butenyl and 2-butenyl.

The term "alkynyl" refers to a straight or branched chain hydrocarbyl radical having at least one carbon-carbon triple bond. Unless otherwise specified, the term "alkynyl" refers to a group having in the range of 2 up to about 12 carbon atoms (for instance, 2 to 10 carbon atoms), e.g., ethynyl, propynyl, and butynyl.

The term "cycloalkyl" denotes a non-aromatic mono or multicyclic ring system of about 3 to 12 carbon atoms such as cyclopropyl, cyclobutyl, cyclopentyl, and cyclohexyl.

The term "cycloalkylalkyl" refers to a cyclic ring-containing radical containing in the range of about 3 up to 8 carbon atoms directly attached to an alkyl group which is then attached to the main structure at any carbon in the alkyl group that results in the creation of a stable structure such as cyclopropylmethyl, cyclobutylethyl, and cyclopentylethyl.

The term "cycloalkenyl" refers to a non-aromatic mono or multicyclic ring system of about 3 to 12 carbon atoms and comprising at least one carbon-carbon double bond within the ring system. Examples of cycloalkenyls include, but are not limited to, cyclopropenyl, cyclobutenyl, cyclopentenyl, cyclohexenyl, and the like.

The term "cycloalkenylalkyl" refers to a radical of the form —$R_aR_b$, wherein $R_a$ is an alkylene group as defined herein and $R_b$ is a cycloalkenyl group as defined herein. Examples of cycloalkenylalkyls include, but are not limited to, cyclopropenylmethyl, cyclobutenylmethyl, cyclopentenymethyl, or cyclohexenylmethyl, and the like.

The term "aryl" refers to a mono- or multi-cyclic aromatic radical having in the range of 6 up to 20 carbon atoms such as phenyl, naphthyl, tetrahydronapthyl, indanyl, and biphenyl.

The term "arylalkyl" refers to an aryl group as defined above directly bonded to an alkyl group as defined above, e.g., —$CH_2C_6H_5$, and —$C_2H_5C_6H_5$.

The term "heterocyclyl" refers to a non-aromatic 3 to 15 member ring radical, which consists of carbon atoms and at least one heteroatom of nitrogen, phosphorus, oxygen or sulfur. The heterocyclic ring radical may be a mono-, bi-, tri- or tetracyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized.

The term "heterocyclylalkyl" refers to a heterocyclyl group as defined above directly bonded to an alkyl group as defined above.

The term "heteroaryl" refers to an optionally substituted 5-14 member aromatic ring having one or more heteroatoms of N, O, or S as ring atoms. The heteroaryl may be a mono-, bi- or tricyclic ring system. Examples of such heteroaryl ring radicals include, but are not limited to, oxazolyl, thiazolyl imidazolyl, pyrrolyl, furanyl, pyridinyl, pyrimidinyl, pyrazinyl, benzofuranyl, indolyl, benzothiazolyl, benzoxazolyl, carbazolyl, quinolyl, and isoquinolyl.

The term "heteroarylalkyl" refers to an heteroaryl group as defined above directly bonded to an alkyl group as defined above, e.g., —$CH_2C_6H_4N$, and —$C_2H_5C_6H_4N$.

The term "halogen" includes F, Cl, Br, and I.

The term "amino acid side chain" refers to the side chain R of an alpha amino acid of the formula $H_2N$—CH(R)—COOH. For example, the side chain of alanine is methyl, the side chain of glycine is hydrogen, the side chain of valine is iso-propyl, and the side chain of tryptophan is (1H-indol-3-yl)methyl. Suitable amino acid side chains in the compounds of the present invention include those of natural amino acids, including proteinogenic amino acids. Non-limiting examples of natural amino acids include standard amino acids or proteinogenic amino acids. Standard amino acids or proteinogenic amino acids include, but are not limited to, alanine, arginine, asparagine, aspartic acid, cysteine, glutamic acid, glutamine, glycine, histidine, isoleucine, leucine, lysine, methionine, phenylalanine, proline, pyrrolysine, selenocysteine, serine, threonine, tryptophan, tyrosine and valine.

The term "PEG" refers to polyethylene glycol.

Unless otherwise specified, all of the above groups are optionally substituted.

The term "substituted", unless otherwise specified, refers to substitution with any one or any combination of the following substituents: hydrogen, hydroxy, halogen, carboxyl, cyano, nitro, oxo (=O), thio(=S), alkyl, alkoxy, alkenyl, alkynyl, aryl, arylalkyl, cycloalkyl, cycloalkenyl, aryl, heterocyclyl, heteroaryl, —$COOR^x$, —$C(O)R^x$, —$C(S)R^x$, —$C(O)NR^xR^y$, —$C(O)ONR^xR^y$, —$NR^yR^z$, —$NR^x$-$CONR^yR^z$, —$N(R^x)SOR^y$, —$N(R^x)SO_2R^y$, —(=N—N($R^x$)

R$^y$), —NR$^x$C(O)OR$^y$, —NR$^x$R$^y$, —NR$^x$C(O)R$^y$—, —NR$^x$C(S)R$^y$—NR$^x$C(S)NR$^y$R$^z$, —SONR$^x$R$^y$—, —SO$_2$NR$^x$R$^y$—, —OR$^x$, —OR$^x$C(O)NR$^y$R$^z$, —OR$^x$C(O)OR$^y$—, —OC(O) R$^x$, —OC(O)NR$^x$R$^y$, —R$^x$NR$^y$C(O)R$^z$, —R$^x$OR$^y$, —R$^x$C(O) OR$^y$, —R$^x$C(O)NR$^y$R$^z$, —R$^x$C(O)R$^x$, —R$^x$OC(O)R$^y$, —SR$^x$, —SOR$^x$, —SO$_2$R$^x$, and —ONO$_2$, wherein R$^x$, R$^y$ and R$^z$ in each of the above groups can be independently hydrogen atom, alkyl, alkoxy, alkenyl, alkynyl, aryl, arylalkyl, cycloalkyl, cycloalkenyl, amino, aryl, heteroaryl, heterocyclyl, or any two of R$^x$, R$^y$ and R$^z$ may be joined to form a saturated or unsaturated 3-10 member ring, which may optionally include heteroatoms which may be same or different and are O, N or S. In one embodiment, the term substituted refers to substitution with one or more halogens (e.g., fluorine).

The term "subject" refers to a mammal, such as a domestic pet (for example, a dog or cat), or human. Preferably, the subject is a human.

The phrase "effective amount" refers to the amount which, when administered to a subject or patient for treating a disease, is sufficient to effect such treatment for the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

The invention disclosed herein is also meant to encompass all pharmaceutically acceptable compounds of the structures disclosed herein being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. Certain isotopically-labelled compounds of structures disclosed herein, for example, those incorporating a radioactive isotope, are useful in drug and/or substrate tissue distribution studies. These radiolabelled compounds could be useful to help determine or measure the effectiveness of the compounds, by characterizing, for example, the site or mode of action, or binding affinity to pharmacologically important site of action. The radioactive isotopes tritium, i.e., $^3$H, and carbon-14, i.e., $^{14}$C, are particularly useful for this purpose in view of their ease of incorporation and ready means of detection.

Substitution with heavier isotopes such as deuterium, i.e., $^2$H, may afford certain therapeutic advantages resulting from greater metabolic stability, for example, increased in vivo half-life or reduced dosage requirements, and hence are preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds can generally be prepared by conventional techniques known to those skilled in the art or by processes analogous to those described in the Preparations and Examples as set out below using an appropriate isotopically-labeled reagent in place of the non-labeled reagent previously employed.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples. "Stable compound" and "stable structure" are meant to indicate a compound that is sufficiently robust to survive isolation to a useful degree of purity from a reaction mixture, and formulation into an efficacious therapeutic agent.

Often crystallizations produce a solvate of the compound of the invention. As used herein, the term "solvate" refers to an aggregate that comprises one or more molecules of a compound of the invention with one or more molecules of solvent. In some embodiments, the solvent is water, in which case the solvate is a hydrate. Alternatively, in other embodiments, the solvent is an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. In some aspects, the compound of the invention is a true solvate, while in other cases, the compound of the invention merely retains adventitious water or is a mixture of water plus some adventitious solvent.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

The term "physiological pH" refers to the pH typically found in the human body or blood (e.g., at a pH of between about 7.3 and about 7.5, such as at a pH of between 7.3 and about 7.4, such as at a pH of about 7.4 or at a pH of about 7.365).

The term "pKa" refers to the negative logarithm of the acidity constant.

The term "dosage unit form" is the form of a pharmaceutical product, including, but not limited to, the form in which the pharmaceutical product is marketed for use. Examples include, but are not limited to, pills, tablets, capsules, and liquid solutions and suspensions.

The compounds of the invention, or their pharmaceutically acceptable salts may contain one or more asymmetric centers and may thus give rise to enantiomers, diastereomers, and other stereoisomeric forms that are defined, in terms of absolute stereochemistry, as (R)- or (S)- or, as (D)- or (L)- for amino acids. The present invention is meant to include all such possible isomers, as well as their racemic and optically pure forms. Optically active (+) and (−). (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

The present invention includes all manner of rotamers and conformationally restricted states of a compound of the invention. Atropisomers, which are stereoisomers arising because of hindered rotation about a single bond, where energy differences due to steric strain or other contributors create a barrier to rotation that is high enough to allow for isolation of individual conformers, are also included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another. For example, in addition to the specifically depicted stereocenter, the carbon atom marked with an "*" in the following structure may be asymmetric and all stereoisomers (R and S) and enantiomeric mixtures of compounds having an asymmetric carbon at this position are also included in the scope of the invention.

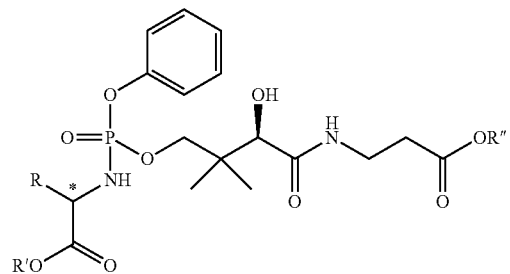

The various substituents (e.g. R, R' and R") also include stereocenters in some embodiments and all such stereocenters and entiomeric mixtures are included in the scope of the present invention.

A "tautomer" refers to a proton shift from one atom of a molecule to another atom of the same molecule. The present invention includes tautomers of any of the disclosed compounds.

Compounds

As noted above, the present invention relates to particular precursor small molecules of 4'-phosphopantothenate or a surrogate for 4'-phosphopantothenate.

In one embodiment, the compounds have the formula (A):

Formula A

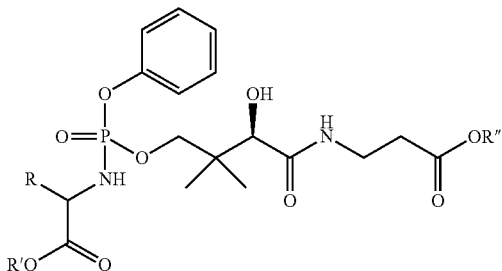

or a pharmaceutically acceptable salt thereof, wherein

R is an amino acid side chain;

R' is hydrogen, substituted or unsubstituted $C_1$-$C_{20}$ alkyl (such as unsubstituted $C_7$-$C_{20}$ alkyl), substituted or unsubstituted $C_7$-$C_{20}$ alkenyl, or substituted and unsubstituted arylalkyl; and R" is hydrogen, substituted or unsubstituted $C_1$-$C_{20}$ alkyl (e.g., $C_1$-$C_8$ alkyl or $C_1$-$C_6$ alkyl), substituted or unsubstituted $C_2$-$C_{20}$ alkenyl (e.g., $C_2$-$C_6$ alkenyl), substituted or unsubstituted alkynyl (e.g., $C_2$-$C_6$ alkynyl), substituted or unsubstituted cycloalkyl (e.g., $C_3$-$C_8$ cycloalkyl), substituted or unsubstituted cycloalkenyl (e.g., $C_3$-$C_8$ cycloalkenyl), substituted or unsubstituted cycloalkylalkyl (e.g., $C_3$-$C_8$ cycloalkyl($C_1$-$C_6$ alkyl)), substituted or unsubstituted cycloalkenylalkyl (e.g., $C_3$-$C_8$ cycloalkenyl($C_1$-$C_6$ alkyl)), substituted or unsubstituted aryl, substituted or unsubstituted arylalkyl, substituted or unsubstituted heterocyclyl, substituted or unsubstituted heteroaryl, substituted or unsubstituted heterocyclylalkyl, substituted or unsubstituted heteroarylalkyl, or PEG (e.g., where the PEG has 2 to 100 repeating units), each of which is optionally substituted by one or more halogen (e.g., fluorine).

In one embodiment, R' is substituted or unsubstituted $C_7$-$C_{20}$ alkyl (such as unsubstituted $C_7$-$C_{20}$ alkyl) or substituted or unsubstituted $C_7$-$C_{20}$ alkenyl.

In one embodiment, R' is $C_8$-$C_{20}$ alkyl (e.g., $C_8$-$C_{12}$ alkyl, $C_8$-$C_{10}$ alkyl, $C_{10}$-$C_{20}$ alkyl, $C_{10}$-$C_{16}$ alkyl or $C_8$-$C_{16}$ alkyl).

In one embodiment, R" is substituted or unsubstituted $C_1$-$C_{20}$ alkyl (e.g., $C_1$-$C_8$ alkyl or $C_1$-$C_6$ alkyl), substituted or unsubstituted $C_2$-$C_{20}$ alkenyl (e.g., $C_2$-$C_6$ alkenyl), substituted or unsubstituted alkynyl (e.g., $C_2$-$C_6$ alkynyl), substituted or unsubstituted cycloalkyl (e.g., $C_3$-$C_8$ cycloalkyl), substituted or unsubstituted cycloalkenyl (e.g., $C_3$-$C_8$ cycloalkenyl), substituted or unsubstituted cycloalkylalkyl (e.g., $C_3$-$C_8$ cycloalkyl($C_1$-$C_6$ alkyl)), substituted or unsubstituted cycloalkenylalkyl (e.g., $C_3$-$C_8$ cycloalkenyl($C_1$-$C_6$ alkyl)), substituted or unsubstituted aryl, substituted or unsubstituted arylalkyl, substituted or unsubstituted heterocyclyl, substituted or unsubstituted heteroaryl, substituted or unsubstituted heterocyclylalkyl, substituted or unsubstituted heteroarylalkyl or PEG (e.g., where the PEG has 2 to 100 repeating units), each of which is optionally substituted by one or more halogen (e.g., fluorine).

In another embodiment, R" is $C_1$-$C_6$ alkyl (e.g., methyl, ethyl, n-propyl, i-propyl, n-butyl, i-butyl, t-butyl, neopentyl), benzyl, cyclohexyl, or methylcyclopropyl.

One embodiment of the invention is a compound of Formula A, or a pharmaceutically acceptable salt, stereoisomer, or tautomer thereof, wherein R is an amino acid side chain;

R' is substituted or unsubstituted $C_7$-$C_{20}$ alkyl or substituted or unsubstituted $C_7$-$C_{20}$ alkenyl; and R" is substituted or unsubstituted $C_1$-$C_{20}$ alkyl, substituted or unsubstituted $C_2$-$C_{20}$ alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted aryl, substituted or unsubstituted arylalkyl, substituted or unsubstituted heterocyclyl, substituted or unsubstituted heteroaryl, substituted or unsubstituted heterocyclylalkyl, substituted or unsubstituted heteroarylalkyl or PEG, each of which is optionally substituted by one or more halogen.

In one embodiment, the amino acid side chain in the definition of R is that of an unnatural amino acid. In one preferred embodiment, the amino acid side chain in the definition of R is that of a natural amino acid (e.g., a natural L-amino acid). R may be attached to the carbon depicted such that the carbon has the R or S absolute configuration (D or L relative configuration). In a more preferred embodiment, R is the side chain of a proteinogenic amino acid. In one preferred embodiment, the stereochemistry of the R group is such that the compound of formula A has the following stereochemistry:

Formula A1

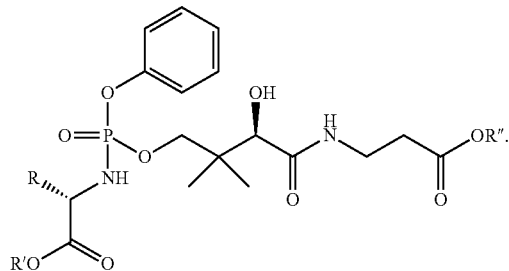

Another embodiment of the invention is a compound having the formula:

Formula A2

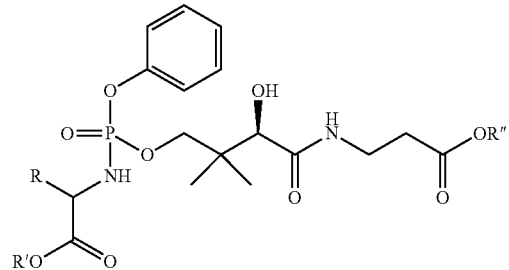

or a pharmaceutically acceptable salt thereof, wherein

R is an amino acid side chain;

R' is hydrogen, substituted or unsubstituted $C_1$-$C_{20}$ alkyl, substituted or unsubstituted $C_7$-$C_{20}$ alkenyl, or substituted and unsubstituted arylalkyl; and R" is hydrogen, substituted or unsubstituted $C_1$-$C_{20}$ alkyl, substituted or unsubstituted $C_2$-$C_{20}$ alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted aryl, substituted or unsubstituted arylalkyl, substituted or unsubstituted heterocyclyl, substituted or unsubstituted heteroaryl, substituted or unsubstituted heterocyclylalkyl, substituted or unsubstituted heteroarylalkyl or PEG, each of which is optionally substituted by one or more halogen; and R, R', and R" are not the following:

| R (Amino Acid) | R' | R" |
|---|---|---|
| Me (L-Ala) | Me | Me |
| Me (L-Ala) | Et | Bn |
| Me (L-Ala) | MeCyPr | MeCyPr |
| MeIndole (L-Trp) | Bn | Et |

Another embodiment of the invention is a compound of formula A or A1, where R is methyl (i.e., the amino acid is alanine), R' is isopropyl, and R" is methyl, ethyl, isopropyl, neopentyl, or benzyl.

Yet another embodiment of the invention is a compound of formula A or A1, where R is methyl (i.e., the amino acid is alanine), R' is neopentyl, and R" is methyl, ethyl, isopropyl, neopentyl, or benzyl.

Yet another embodiment of the invention is a compound of formula A or A1 where R, R' and R" are as defined in the table below (Table 1).

TABLE 1

| Compound No. | AA (R) | R' | R" |
|---|---|---|---|
| 1 | L-Ala (R = Me) | Me | iPr |
| 2 | L-Ala (R = Me) | Et | iPr |
| 3 | L-Ala (R = Me) | iPr | iPr |
| 4 | L-Ala (R = Me) | neoPent | iPr |
| 5 | L-Ala (R = Me) | Bn | iPr |
| 6 | L-Ala (R = Me) | neoPent | Me |
| 7 | L-Ala (R = Me) | neoPent | Et |
| 8 | L-Ala (R = Me) | neoPent | iPr |
| 9 | L-Ala (R = Me) | neoPent | neoPent |
| 10 | L-Ala (R = Me) | neoPent | Bn |
| 11 | L-Val (R = iPr) | Me | iPr |
| 12 | L-Val (R = iPr) | Et | iPr |
| 13 | L-Val (R = iPr) | iPr | iPr |
| 14 | L-Val (R = iPr) | neoPent | iPr |
| 15 | L-Val (R = iPr) | Bn | iPr |
| 16 | L-Val (R = iPr) | neoPent | Me |
| 17 | L-Val (R = iPr) | neoPent | Et |
| 18 | L-Val (R = iPr) | neoPent | iPr |
| 19 | L-Val (R = iPr) | neoPent | neoPent |
| 20 | L-Val (R = iPr) | neoPent | Bn |
| 21 | L-Val (R = iPr) | Me | Me |
| 22 | L-Ala (R = Me) | Me | Bn |
| 23 | L-Ala (R = Me) | iPr | neoPent |
| 24 | L-Ala (R = Me) | Bn | Me |
| 25 | L-Ala (R = Me) | iBu | iBu |
| 26 | L-Ala (R = Me) | iPr | Et |
| 27 | L-Phe (R = Bn) | Bn | Me |
| 28 | L-Ala (R = Me) | iPr | Me |
| 29 | L-Ala (R = Me) | H | Me |
| 30 | L-Ala (R = Me) | Me | H |

(wherein AA represents the amino acid from which the side chain "R" is derived, Et is ethyl, Me is methyl, n Bu is n-butyl, iPr is isopropyl, neoPent is neopentyl, Bn is benzyl, iBu is isobutyl, L-Ala is L-alanine, Gly is glycine, L-Trp is L-tryptophan, L-Val is L-valine, and L-Phe is L-phenylalanine).

Still other embodiments provide a compound having the following formula (B):

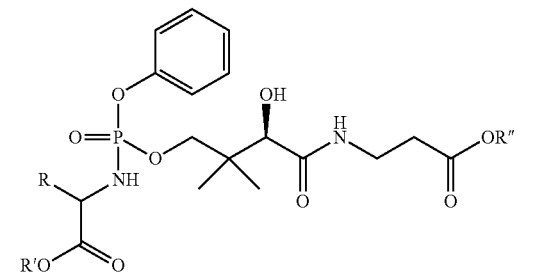

Formula B or a pharmaceutically acceptable salt thereof, wherein R is methyl, R' is isopropyl, and R" is methyl, ethyl, isopropyl, neopentyl, or benzyl.

Yet another embodiment provides a compound having the following formula (C):

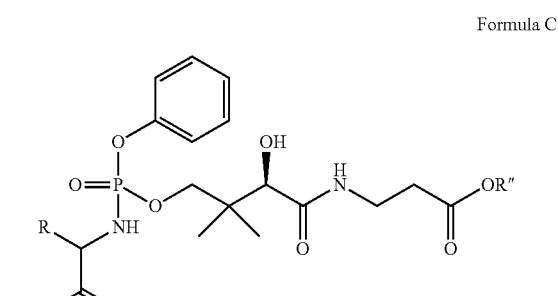

Formula C or a pharmaceutically acceptable salt thereof, wherein R is methyl, R' is neopentyl, and R" is methyl, ethyl, isopropyl, neopentyl, or benzyl.

In still other embodiments are directed to a compound having the following formula (D):

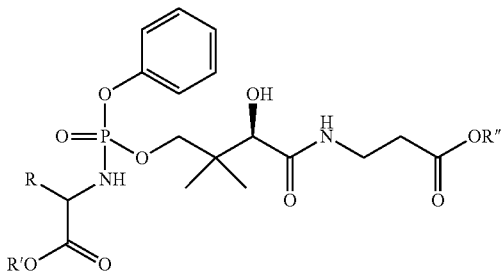

Formula D or a pharmaceutically acceptable salt thereof, wherein R, R' and R" are as defined in Table 1 herein.

Yet another embodiment of the invention is a compound having the formula:

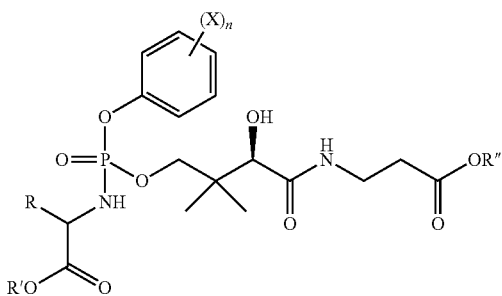

Formula E or a pharmaceutically acceptable salt thereof, wherein

R is an amino acid side chain;

each occurrence of X is, independently, halogen (e.g., Cl or F), alkyl (e.g., $C_{1-8}$ alkyl, $C_{1-6}$ alkyl, or $C_{1-4}$ alkyl), alkenyl (e.g., $C_{1-8}$ alkenyl, $C_{1-6}$ alkenyl, or $C_{1-4}$ alkenyl), halogenated alkyl (e.g., $C_1$-$C_6$ alkyl such as —$CF_3$), —CN, —$NO_2$, —$C(O)_2R^1$, —$C(O)R^1$, or —$OR^2$;

n is 1, 2, 3, 4 or 5 (e.g., 1 or 2);

each occurrence of $R^1$ is, independently, $C_{1-6}$ alkyl (e.g., methyl or ethyl);

each occurrence of $R^2$ is, independently, $C_{1-6}$ alkyl (e.g., methyl or ethyl), $C_2$-$C_6$ alkenyl, $C_2$-$C_6$ alkynyl, aryl or polyethylene glycol (PEG) (e.g., where the PEG has 2 to 100 repeating units);

R' is substituted or unsubstituted $C_1$-$C_{20}$ alkyl (e.g., $C_1$-$C_8$ alkyl or $C_1$-$C_6$ alkyl), substituted or unsubstituted $C_2$-$C_{20}$ alkenyl (e.g., $C_2$-$C_6$ alkenyl), substituted or unsubstituted alkynyl (e.g., $C_2$-$C_6$ alkynyl), substituted or unsubstituted cycloalkyl (e.g., $C_3$-$C_8$ cycloalkyl), substituted or unsubstituted cycloalkenyl (e.g., $C_3$-$C_8$ cycloalkenyl), substituted or unsubstituted cycloalkylalkyl (e.g., $C_3$-$C_8$ cycloalkyl($C_1$-$C_6$ alkyl)), substituted or unsubstituted cycloalkenylalkyl (e.g., $C_3$-$C_8$ cycloalkenyl($C_1$-$C_6$ alkyl)), substituted or unsubstituted aryl, substituted or unsubstituted arylalkyl, substituted or unsubstituted heterocyclyl, substituted or unsubstituted heteroaryl, substituted or unsubstituted heteroarylalkyl, each of which is optionally substituted by one or more halogen (e.g., fluorine); and R" is substituted or unsubstituted $C_1$-$C_{20}$ alkyl (e.g., $C_1$-$C_8$ alkyl or $C_1$-$C_6$ alkyl), substituted or unsubstituted $C_2$-$C_{20}$ alkenyl (e.g., $C_2$-$C_6$ alkenyl), substituted or unsubstituted alkynyl (e.g., $C_2$-$C_6$ alkynyl), substituted or unsubstituted cycloalkyl (e.g., $C_3$-$C_8$ cycloalkyl), substituted or unsubstituted cycloalkenyl (e.g., $C_3$-$C_8$ cycloalkenyl), substituted or unsubstituted cycloalkylalkyl (e.g., $C_3$-$C_8$ cycloalkyl($C_1$-$C_6$ alkyl)), substituted or unsubstituted cycloalkenylalkyl (e.g., $C_3$-$C_8$ cycloalkenyl($C_1$-$C_6$ alkyl)), substituted or unsubstituted aryl, substituted or unsubstituted arylalkyl, substituted or unsubstituted heterocyclyl, substituted or unsubstituted heteroaryl, substituted or unsubstituted heterocyclylalkyl, substituted or unsubstituted heteroarylalkyl or PEG (e.g., where the PEG has 2 to 100 repeating units), each of which is optionally substituted by one or more halogen (e.g., fluorine).

In some embodiments, each occurrence of X is, independently, halogen (e.g., Cl or F), alkyl (e.g., $C_{1-8}$ alkyl, $C_{1-6}$ alkyl, or $C_{1-4}$ alkyl), alkenyl (e.g., $C_{1-8}$ alkenyl, $C_{1-6}$ alkenyl, or $C_{1-4}$ alkenyl), halogenated alkyl (e.g., $C_1$-$C_6$ alkyl such as —$CF_3$), —CN, —$NO_2$, —$C(O)_2R^1$, —$C(O)R^1$, or —$OR^2$, wherein at least one occurrence of X is not halogen.

In one preferred embodiment, n is 1. In another preferred embodiment n is 2.

In another embodiment, each occurrence of X is, independently, halogen (e.g., Cl or F), halogenated alkyl (e.g., $C_1$-$C_6$ alkyl such as —$CF_3$), —CN, —$NO_2$, —$C(O)_2R^1$, or —$C(O)R^1$, wherein at least one occurrence of X is not halogen.

In one embodiment, the amino acid side chain in the definition of R is that of an unnatural amino acid. In one preferred embodiment, the amino acid side chain in the definition of R is that of a natural amino acid (e.g., a natural L-amino acid). R may be attached to the carbon depicted such that the carbon has the R or S absolute configuration (D or L relative configuration). In a more preferred embodiment, R is the side chain of a proteinogenic amino acid.

In some embodiments, R is H, $C_1$-$C_6$ alkyl, or heteroarylalkyl. For example, in some embodiments, R is $C_1$-$C_6$ alkyl, such as methyl or isopropyl. In other embodiments, R is H. In still more embodiments, R is heteroarylalkyl, such as (1H-indol-3-yl)methyl.

In one preferred embodiment, the stereochemistry of the R group is such that the compound of formula E has the following stereochemistry:

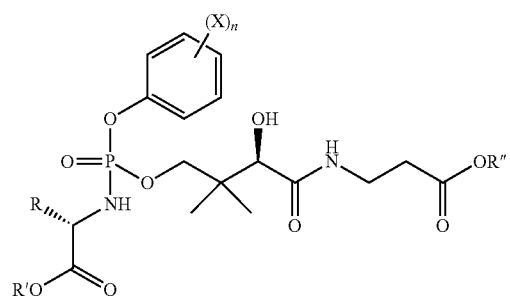

Formula E1 where R, R', R", X, and n are as defined with respect to formula E above.

In some embodiments, R' is $C_1$-$C_6$ alkyl, aralkyl, cycloalkyl, or cycloalkylalkyl, each of which is optionally substituted by one or more halogen. In some of these embodiments, $C_1$-$C_6$ alkyl is methyl, ethyl, isopropyl, n-butyl, or neopentyl.

In one embodiment of the compound of formula A, A1, E, or E1, R' is $C_1$-$C_6$ alkyl (e.g., methyl, ethyl, n-propyl, i-propyl, n-butyl, i-butyl, neopentyl or t-butyl), benzyl, cyclohexyl, or methylcyclopropyl, each of which is optionally substituted by one or more halogen (e.g., fluorine).

In other embodiments. R" is $C_1$-$C_6$ alkyl, aralkyl, cycloalkyl, or cycloalkylalkyl, each of which is optionally substituted by one or more halogen. In some of these embodiments, $C_1$-$C_6$ alkyl is methyl, ethyl, isopropyl, n-butyl, or neopentyl.

In one embodiment of the compound of formula A, A1, E, or E1, R" is $C_1$-$C_6$ alkyl (e.g., methyl, ethyl, n-propyl, i-propyl, n-butyl, i-butyl, neopentyl or t-butyl), benzyl, cyclohexyl, or methylcyclopropyl, each of which is optionally substituted by one or more halogen (e.g., fluorine).

In one embodiment of the compound of formula E or E1, each occurrence of X is, independently, Cl (e.g., m-Cl, p-Cl), F (e.g., m-F, p-F), —$CF_3$ (e.g., m-$CF_3$), —CN (e.g., p-CN), —$NO_2$ (e.g., p-$NO_2$), —$C(O)_2Me$ (e.g., p-$C(O)_2Me$) or —C(O)Me (e.g., m-C(O)Me, p-C(O)Me).

In one embodiment, the compound of Formula E has the formula E2 or E3:

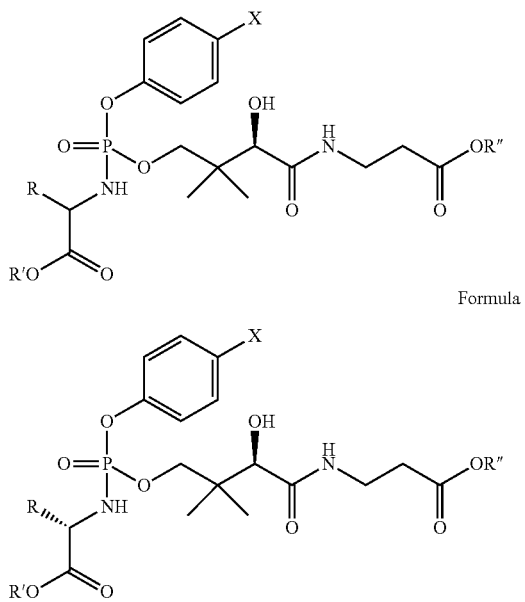

Formula E2

Formula E3 where R, R', R", and X are as defined with respect to formula E above.

In some further embodiments, R is methyl, hydrogen, (1H-indol-3-yl)methyl, or isopropyl;
n is 1:
X is Cl, F, —CN, —$NO_2$, —$C(O)_2R^1$, or —$C(O)R^1$;
$R^1$ is Me;
R' is methyl, ethyl, n-butyl, benzyl, methylcylopropyl, isopropyl, or neopentyl; and
R" is methyl, ethyl, n-butyl, benzyl, methylcylopropyl, isopropyl, or neopentyl.

In one embodiment of the compound of formula E2 or E3, R' is $C_1$-$C_6$ alkyl (e.g., methyl, ethyl, n-propyl, i-propyl, n-butyl, i-butyl, neopentyl or t-butyl), benzyl, cyclohexyl, or methylcyclopropyl, each of which is optionally substituted by one or more halogen (e.g., fluorine).

In one embodiment of the compound of formula E2 or E3, R" is $C_1$-$C_6$ alkyl (e.g., methyl, ethyl, n-propyl, i-propyl, n-butyl, i-butyl, neopentyl or t-butyl), benzyl, cyclohexyl, or methylcyclopropyl, each of which is optionally substituted by one or more halogen (e.g., fluorine).

Representative compounds of the present invention of formulas E2 and E3 are depicted in Table 2 below:

TABLE 2

| Compound No. | AA (R) | R' | R" | X |
|---|---|---|---|---|
| 31 | L-Ala (R = Me) | Et | Et | p-$NO_2$ |
| 32 | L-Ala (R = Me) | Et | Et | p-CN |
| 33 | L-Ala (R = Me) | Et | Et | p-COOMe |
| 34 | L-Ala (R = Me) | Et | Et | p-COMe |
| 35 | L-Ala (R = Me) | Et | Et | p-Cl |
| 36 | L-Ala (R = Me) | Et | Et | p-F |
| 37 | L-Ala (R = Me) | Me | Me | p-$NO_2$ |
| 38 | L-Ala (R = Me) | Me | Me | p-CN |
| 39 | L-Ala (R = Me) | Me | Me | p-COOMe |
| 40 | L-Ala (R = Me) | Me | Me | p-COMe |
| 41 | L-Ala (R = Me) | Me | Me | p-Cl |
| 42 | L-Ala (R = Me) | Me | Me | p-F |
| 43 | L-Ala (R = Me) | n Bu | n Bu | p-$NO_2$ |
| 44 | L-Ala (R = Me) | n Bu | n Bu | p-CN |
| 45 | L-Ala (R = Me) | n Bu | n Bu | p-COOMe |
| 46 | L-Ala (R = Me) | n Bu | n Bu | p-COMe |
| 47 | L-Ala (R = Me) | n Bu | n Bu | p-Cl |
| 48 | L-Ala (R = Me) | n Bu | n Bu | p-F |
| 49 | L-Ala (R = Me) | Bn | Et | p-$NO_2$ |
| 50 | L-Ala (R = Me) | Bn | Et | p-CN |
| 51 | L-Ala (R = Me) | Bn | Et | p-COOMe |
| 52 | L-Ala (R = Me) | Bn | Et | p-COMe |
| 53 | L-Ala (R = Me) | Bn | Et | p-Cl |
| 54 | L-Ala (R = Me) | Bn | Et | p-F |
| 55 | L-Ala (R = Me) | Et | Bn | p-$NO_2$ |
| 56 | L-Ala (R = Me) | Et | Bn | p-CN |
| 57 | L-Ala (R = Me) | Et | Bn | p-COOMe |
| 58 | L-Ala (R = Me) | Et | Bn | p-COMe |
| 59 | L-Ala (R = Me) | Et | Bn | p-Cl |
| 60 | L-Ala (R = Me) | Et | Bn | p-F |
| 61 | L-Ala (R = Me) | Bn | Bn | p-$NO_2$ |
| 62 | L-Ala (R = Me) | Bn | Bn | p-CN |

TABLE 2-continued

| Compound No. | AA (R) | R' | R" | X |
|---|---|---|---|---|
| 63 | L-Ala (R = Me) | Bn | Bn | p-COOMe |
| 64 | L-Ala (R = Me) | Bn | Bn | p-COMe |
| 65 | L-Ala (R = Me) | Bn | Bn | p-Cl |
| 66 | L-Ala (R = Me) | Bn | Bn | p-F |
| 67 | L-Ala (R = Me) | MeCyPr | MeCyPr | p-NO$_2$ |
| 68 | L-Ala (R = Me) | MeCyPr | MeCyPr | p-CN |
| 69 | L-Ala (R = Me) | MeCyPr | MeCyPr | p-COOMe |
| 70 | L-Ala (R = Me) | MeCyPr | MeCyPr | p-COMe |
| 71 | L-Ala (R = Me) | MeCyPr | MeCyPr | p-Cl |
| 72 | L-Ala (R = Me) | MeCyPr | MeCyPr | p-F |
| 73 | L-Ala (R = Me) | Me | iPr | p-NO$_2$ |
| 74 | L-Ala (R = Me) | Me | iPr | p-CN |
| 75 | L-Ala (R = Me) | Me | iPr | p-COOMe |
| 76 | L-Ala (R = Me) | Me | iPr | p-COMe |
| 77 | L-Ala (R = Me) | Me | iPr | p-Cl |
| 78 | L-Ala (R = Me) | Me | iPr | p-F |
| 79 | L-Ala (R = Me) | Et | iPr | p-NO$_2$ |
| 80 | L-Ala (R = Me) | Et | iPr | p-CN |
| 81 | L-Ala (R = Me) | Et | iPr | p-COOMe |
| 82 | L-Ala (R = Me) | Et | iPr | p-COMe |
| 83 | L-Ala (R = Me) | Et | iPr | p-Cl |
| 84 | L-Ala (R = Me) | Et | iPr | p-F |
| 85 | L-Ala (R = Me) | iPr | iPr | p-NO$_2$ |
| 86 | L-Ala (R = Me) | iPr | iPr | p-CN |
| 87 | L-Ala (R = Me) | iPr | iPr | p-COOMe |
| 88 | L-Ala (R = Me) | iPr | iPr | p-COMe |
| 89 | L-Ala (R = Me) | iPr | iPr | p-Cl |
| 90 | L-Ala (R = Me) | iPr | iPr | p-F |
| 91 | L-Ala (R = Me) | neoPent | iPr | p-NO$_2$ |
| 92 | L-Ala (R = Me) | neoPent | iPr | p-CN |
| 93 | L-Ala (R = Me) | neoPent | iPr | p-COOMe |
| 94 | L-Ala (R = Me) | neoPent | iPr | p-COMe |
| 95 | L-Ala (R = Me) | neoPent | iPr | p-Cl |
| 96 | L-Ala (R = Me) | neoPent | iPr | p-F |
| 97 | L-Ala (R = Me) | Bn | iPr | p-NO$_2$ |
| 98 | L-Ala (R = Me) | Bn | iPr | p-CN |
| 99 | L-Ala (R = Me) | Bn | iPr | p-COOMe |
| 100 | L-Ala (R = Me) | Bn | iPr | p-COMe |
| 101 | L-Ala (R = Me) | Bn | iPr | p-Cl |
| 102 | L-Ala (R = Me) | Bn | iPr | p-F |
| 103 | L-Ala (R = Me) | neoPent | Me | p-NO$_2$ |
| 104 | L-Ala (R = Me) | neoPent | Me | p-CN |
| 105 | L-Ala (R = Me) | neoPent | Me | p-COOMe |
| 106 | L-Ala (R = Me) | neoPent | Me | p-COMe |
| 107 | L-Ala (R = Me) | neoPent | Me | p-Cl |
| 108 | L-Ala (R = Me) | neoPent | Me | p-F |
| 109 | L-Ala (R = Me) | neoPent | Et | p-NO$_2$ |
| 110 | L-Ala (R = Me) | neoPent | Et | p-CN |
| 111 | L-Ala (R = Me) | neoPent | Et | p-COOMe |
| 112 | L-Ala (R = Me) | neoPent | Et | p-COMe |
| 113 | L-Ala (R = Me) | neoPent | Et | p-Cl |
| 114 | L-Ala (R = Me) | neoPent | Et | p-F |
| 115 | L-Ala (R = Me) | neoPent | iPr | p-NO$_2$ |
| 116 | L-Ala (R = Me) | neoPent | iPr | p-CN |
| 117 | L-Ala (R = Me) | neoPent | iPr | p-COOMe |
| 118 | L-Ala (R = Me) | neoPent | iPr | p-COMe |
| 119 | L-Ala (R = Me) | neoPent | iPr | p-Cl |
| 120 | L-Ala (R = Me) | neoPent | iPr | p-F |
| 121 | L-Ala (R = Me) | neoPent | neoPent | p-NO$_2$ |
| 122 | L-Ala (R = Me) | neoPent | neoPent | p-CN |
| 123 | L-Ala (R = Me) | neoPent | neoPent | p-COOMe |
| 124 | L-Ala (R = Me) | neoPent | neoPent | p-COMe |
| 125 | L-Ala (R = Me) | neoPent | neoPent | p-Cl |
| 126 | L-Ala (R = Me) | neoPent | neoPent | p-F |
| 127 | L-Ala (R = Me) | neoPent | Bn | p-NO$_2$ |
| 128 | L-Ala (R = Me) | neoPent | Bn | p-CN |
| 129 | L-Ala (R = Me) | neoPent | Bn | p-COOMe |
| 130 | L-Ala (R = Me) | neoPent | Bn | p-COMe |
| 131 | L-Ala (R = Me) | neoPent | Bn | p-Cl |
| 132 | L-Ala (R = Me) | neoPent | Bn | p-F |
| 133 | Gly (R = H) | Et | Et | p-NO$_2$ |
| 134 | Gly (R = H) | Et | Et | p-CN |
| 135 | Gly (R = H) | Et | Et | p-COOMe |
| 136 | Gly (R = H) | Et | Et | p-COMe |
| 137 | Gly (R = H) | Et | Et | p-Cl |
| 138 | Gly (R = H) | Et | Et | p-F |

TABLE 2-continued

| Compound No. | AA (R) | R' | R" | X |
|---|---|---|---|---|
| 139 | Gly (R = H) | Bn | Bn | p-NO$_2$ |
| 140 | Gly (R = H) | Bn | Bn | p-CN |
| 141 | Gly (R = H) | Bn | Bn | p-COOMe |
| 142 | Gly (R = H) | Bn | Bn | p-COMe |
| 143 | Gly (R = H) | Bn | Bn | p-Cl |
| 144 | Gly (R = H) | Bn | Bn | p-F |
| 145 | Gly (R = H) | Bn | Et | p-NO$_2$ |
| 146 | Gly (R = H) | Bn | Et | p-CN |
| 147 | Gly (R = H) | Bn | Et | p-COOMe |
| 148 | Gly (R = H) | Bn | Et | p-COMe |
| 149 | Gly (R = H) | Bn | Et | p-Cl |
| 150 | Gly (R = H) | Bn | Et | p-F |
| 151 | Gly (R = H) | Et | Bn | p-NO$_2$ |
| 152 | Gly (R = H) | Et | Bn | p-CN |
| 153 | Gly (R = H) | Et | Bn | p-COOMe |
| 154 | Gly (R = H) | Et | Bn | p-COMe |
| 155 | Gly (R = H) | Et | Bn | p-Cl |
| 156 | Gly (R = H) | Et | Bn | p-F |
| 157 | L-Trp (R = (1H-indol-3-yl)methyl) | Me | Me | p-NO$_2$ |
| 158 | L-Trp (R = (1H-indol-3-yl)methyl) | Me | Me | p-CN |
| 159 | L-Trp (R = (1H-indol-3-yl)methyl) | Me | Me | p-COOMe |
| 160 | L-Trp (R = (1H-indol-3-yl)methyl) | Me | Me | p-COMe |
| 161 | L-Trp (R = (1H-indol-3-yl)methyl) | Me | Me | p-Cl |
| 162 | L-Trp (R = (1H-indol-3-yl)methyl) | Me | Me | p-F |
| 163 | L-Trp (R = (1H-indol-3-yl)methyl) | Et | Et | p-NO$_2$ |
| 164 | L-Trp (R = (1H-indol-3-yl)methyl) | Et | Et | p-CN |
| 165 | L-Trp (R = (1H-indol-3-yl)methyl) | Et | Et | p-COOMe |
| 166 | L-Trp (R = (1H-indol-3-yl)methyl) | Et | Et | p-COMe |
| 167 | L-Trp (R = (1H-indol-3-yl)methyl) | Et | Et | p-Cl |
| 168 | L-Trp (R = (1H-indol-3-yl)methyl) | Et | Et | p-F |
| 169 | L-Trp (R = (1H-indol-3-yl)methyl) | Bn | Et | p-NO$_2$ |
| 170 | L-Trp (R = (1H-indol-3-yl)methyl) | Bn | Et | p-CN |
| 171 | L-Trp (R = (1H-indol-3-yl)methyl) | Bn | Et | p-COOMe |
| 172 | L-Trp (R = (1H-indol-3-yl)methyl) | Bn | Et | p-COMe |
| 173 | L-Trp (R = (1H-indol-3-yl)methyl) | Bn | Et | p-Cl |
| 174 | L-Trp (R = (1H-indol-3-yl)methyl) | Bn | Et | p-F |
| 175 | L-Trp (R = (1H-indol-3-yl)methyl) | Et | Bn | p-NO$_2$ |
| 176 | L-Trp (R = (1H-indol-3-yl)methyl) | Et | Bn | p-CN |
| 177 | L-Trp (R = (1H-indol-3-yl)methyl) | Et | Bn | p-COOMe |
| 178 | L-Trp (R = (1H-indol-3-yl)methyl) | Et | Bn | p-COMe |
| 179 | L-Trp (R = (1H-indol-3-yl)methyl) | Et | Bn | p-Cl |
| 180 | L-Trp (R = (1H-indol-3-yl)methyl) | Et | Bn | p-F |
| 181 | L-Trp (R = (1H-indol-3-yl)methyl) | Bn | Bn | p-NO$_2$ |
| 182 | L-Trp (R = (1H-indol-3-yl)methyl) | Bn | Bn | p-CN |
| 183 | L-Trp (R = (1H-indol-3-yl)methyl) | Bn | Bn | p-COOMe |
| 184 | L-Trp (R = (1H-indol-3-yl)methyl) | Bn | Bn | p-COMe |
| 185 | L-Trp (R = (1H-indol-3-yl)methyl) | Bn | Bn | p-Cl |
| 186 | L-Trp (R = (1H-indol-3-yl)methyl) | Bn | Bn | p-F |
| 187 | L-Val (R = iPr) | Me | iPr | p-NO$_2$ |
| 188 | L-Val (R = iPr) | Me | iPr | p-CN |
| 189 | L-Val (R = iPr) | Me | iPr | p-COOMe |
| 190 | L-Val (R = iPr) | Me | iPr | p-COMe |
| 191 | L-Val (R = iPr) | Me | iPr | p-Cl |
| 192 | L-Val (R = iPr) | Me | iPr | p-F |
| 193 | L-Val (R = iPr) | Et | iPr | p-NO$_2$ |
| 194 | L-Val (R = iPr) | Et | iPr | p-CN |
| 195 | L-Val (R = iPr) | Et | iPr | p-COOMe |
| 196 | L-Val (R = iPr) | Et | iPr | p-COMe |
| 197 | L-Val (R = iPr) | Et | iPr | p-Cl |
| 198 | L-Val (R = iPr) | Et | iPr | p-F |
| 199 | L-Val (R = iPr) | iPr | iPr | p-NO$_2$ |

TABLE 2-continued

| Compound No. | AA (R) | R' | R" | X |
|---|---|---|---|---|
| 200 | L-Val (R = iPr) | iPr | iPr | p-CN |
| 201 | L-Val (R = iPr) | iPr | iPr | p-COOMe |
| 202 | L-Val (R = iPr) | iPr | iPr | p-COMe |
| 203 | L-Val (R = iPr) | iPr | iPr | p-Cl |
| 204 | L-Val (R = iPr) | iPr | iPr | p-F |
| 205 | L-Val (R = iPr) | neoPent | iPr | p-NO$_2$ |
| 206 | L-Val (R = iPr) | neoPent | iPr | p-CN |
| 207 | L-Val (R = iPr) | neoPent | iPr | p-COOMe |
| 208 | L-Val (R = iPr) | neoPent | iPr | p-COMe |
| 209 | L-Val (R = iPr) | neoPent | iPr | p-Cl |
| 210 | L-Val (R = iPr) | neoPent | iPr | p-F |
| 211 | L-Val (R = iPr) | Bn | iPr | p-NO$_2$ |
| 212 | L-Val (R = iPr) | Bn | iPr | p-CN |
| 213 | L-Val (R = iPr) | Bn | iPr | p-COOMe |
| 214 | L-Val (R = iPr) | Bn | iPr | p-COMe |
| 215 | L-Val (R = iPr) | Bn | iPr | p-Cl |
| 216 | L-Val (R = iPr) | Bn | iPr | p-F |
| 217 | L-Val (R = iPr) | neoPent | Me | p-NO$_2$ |
| 218 | L-Val (R = iPr) | neoPent | Me | p-CN |
| 219 | L-Val (R = iPr) | neoPent | Me | p-COOMe |
| 220 | L-Val (R = iPr) | neoPent | Me | p-COMe |
| 221 | L-Val (R = iPr) | neoPent | Me | p-Cl |
| 222 | L-Val (R = iPr) | neoPent | Me | p-F |
| 223 | L-Val (R = iPr) | neoPent | Et | p-NO$_2$ |
| 224 | L-Val (R = iPr) | neoPent | Et | p-CN |
| 225 | L-Val (R = iPr) | neoPent | Et | p-COOMe |
| 226 | L-Val (R = iPr) | neoPent | Et | p-COMe |
| 227 | L-Val (R = iPr) | neoPent | Et | p-Cl |
| 228 | L-Val (R = iPr) | neoPent | Et | p-F |
| 229 | L-Val (R = iPr) | neoPent | iPr | p-NO$_2$ |
| 230 | L-Val (R = iPr) | neoPent | iPr | p-CN |
| 231 | L-Val (R = iPr) | neoPent | iPr | p-COOMe |
| 232 | L-Val (R = iPr) | neoPent | iPr | p-COMe |
| 233 | L-Val (R = iPr) | neoPent | iPr | p-Cl |
| 234 | L-Val (R = iPr) | neoPent | iPr | p-F |
| 235 | L-Val (R = iPr) | neoPent | neoPent | p-NO$_2$ |
| 236 | L-Val (R = iPr) | neoPent | neoPent | p-CN |
| 237 | L-Val (R = iPr) | neoPent | neoPent | p-COOMe |
| 238 | L-Val (R = iPr) | neoPent | neoPent | p-COMe |
| 239 | L-Val (R = iPr) | neoPent | neoPent | p-Cl |
| 240 | L-Val (R = iPr) | neoPent | neoPent | p-F |
| 241 | L-Val (R = iPr) | neoPent | Bn | p-NO$_2$ |
| 242 | L-Val (R = iPr) | neoPent | Bn | p-CN |
| 243 | L-Val (R = iPr) | neoPent | Bn | p-COOMe |
| 244 | L-Val (R = iPr) | neoPent | Bn | p-COMe |
| 245 | L-Val (R = iPr) | neoPent | Bn | p-Cl |
| 246 | L-Val (R = iPr) | neoPent | Bn | p-F |
| 247 | L-Val (R = iPr) | Et | Et | p-NO$_2$ |
| 248 | L-Val (R = iPr) | Et | Et | p-CN |
| 249 | L-Val (R = iPr) | Et | Et | p-COOMe |
| 250 | L-Val (R = iPr) | Et | Et | p-COMe |
| 251 | L-Val (R = iPr) | Et | Et | p-Cl |
| 252 | L-Val (R = iPr) | Et | Et | p-F |
| 253 | L-Ala (R = Me) | Bn | Bn | p-OMe |
| 254 | L-Ala (R = Me) | Bn | Et | p-OMe |
| 255 | L-Ala (R = Me) | Me | Me | p-OMe |
| 256 | L-Ala (R = Me) | Et | Et | p-OMe |
| 257 | L-Ala (R = Me) | Et | Bn | p-OMe |

(wherein wherein AA represents the amino acid from which the side chain "R" is derived, Et is ethyl, Me is methyl, nBu is n-butyl, MeCyPr is methylcyclopropyl (i.e., —CH$_2$-cyclopropyl), Bn is benzyl, iPr is isopropyl, neoPent is neopentyl, L-Ala is L-alanine, Gly is glycine, L-Trp is L-tryptophan, and L-Val is L-valine).

In another embodiment, the compound of Formula E is of Formula E4 or E5:

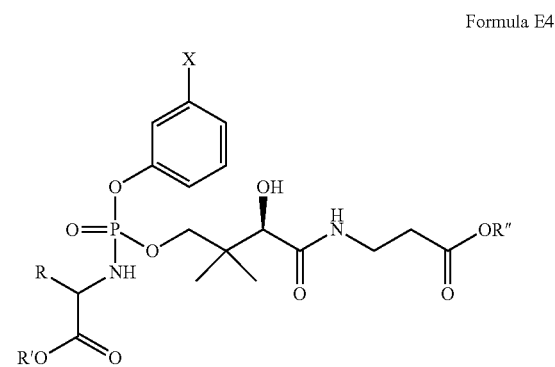

Formula E4

-continued

Formula E5

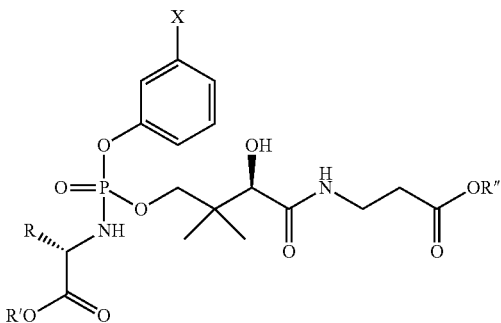

where R, R', R", and X are as defined with respect to formula E above.

In one embodiment of the compound of formula E4 or E5:
R is hydrogen, methyl, isopropyl or (1H-indol-3-yl) methyl;
n is 1;
X is Cl, F, —$CF_3$, or —$C(O)R^1$;
$R^1$ is Me:
R' is methyl, ethyl, n-butyl, benzyl, methylcylopropyl, isopropyl, or neopentyl; and
R" is methyl, ethyl, n-butyl, benzyl, methylcylopropyl, isopropyl, or neopentyl.

In one embodiment of the compound of formula E4 or E5, R' is $C_1$-$C_6$ alkyl (e.g., methyl, ethyl, n-prop, methyl, i-propyl, n-butyl, i-butyl, neopentyl or t-butyl), benzyl, cyclohexyl, or methylcyclopropyl, each of which is optionally substituted by one or more halogen (e.g., fluorine).

In one embodiment of the compound of formula E4 or E5, R" is $C_1$-$C_6$ alkyl (e.g., methyl, ethyl, n-propyl, i-propyl, n-butyl, i-butyl, neopentyl or t-butyl), benzyl, cyclohexyl, or methylcyclopropyl, each of which is optionally substituted by one or more halogen (e.g., fluorine).

Representative compounds of the present invention of formula E4 and E5 are depicted in Table 3 below:

TABLE 3

| Compound No. | AA (R) | R' | R" | X |
|---|---|---|---|---|
| 258 | L-Ala (R = Me) | Et | Et | m-F |
| 259 | L-Ala (R = Me) | Et | Et | m-COMe |
| 260 | L-Ala (R = Me) | Et | Et | m-Cl |
| 261 | L-Ala (R = Me) | Et | Et | m-$CF_3$ |
| 262 | L-Ala (R = Me) | Me | Me | m-F |
| 263 | L-Ala (R = Me) | Me | Me | m-COMe |
| 264 | L-Ala (R = Me) | Me | Me | m-Cl |
| 265 | L-Ala (R = Me) | Me | Me | m-$CF_3$ |
| 266 | L-Ala (R = Me) | n Bu | n Bu | m-F |
| 267 | L-Ala (R = Me) | n Bu | n Bu | m-COMe |
| 268 | L-Ala (R = Me) | n Bu | n Bu | m-Cl |
| 269 | L-Ala (R = Me) | n Bu | n Bu | m-$CF_3$ |
| 270 | L-Ala (R = Me) | Bn | Et | m-F |
| 271 | L-Ala (R = Me) | Bn | Et | m-COMe |
| 272 | L-Ala (R = Me) | Bn | Et | m-Cl |
| 273 | L-Ala (R = Me) | Bn | Et | m-$CF_3$ |
| 274 | L-Ala (R = Me) | Et | Bn | m-F |
| 275 | L-Ala (R = Me) | Et | Bn | m-COMe |
| 276 | L-Ala (R = Me) | Et | Bn | m-Cl |
| 277 | L-Ala (R = Me) | Et | Bn | m-$CF_3$ |
| 278 | L-Ala (R = Me) | Bn | Bn | m-F |
| 279 | L-Ala (R = Me) | Bn | Bn | m-COMe |
| 280 | L-Ala (R = Me) | Bn | Bn | m-Cl |
| 281 | L-Ala (R = Me) | Bn | Bn | m-$CF_3$ |
| 282 | L-Ala (R = Me) | MeCyPr | MeCyPr | m-F |
| 283 | L-Ala (R = Me) | MeCyPr | MeCyPr | m-COMe |
| 284 | L-Ala (R = Me) | MeCyPr | MeCyPr | m-Cl |
| 285 | L-Ala (R = Me) | MeCyPr | MeCyPr | m-$CF_3$ |
| 286 | L-Ala (R = Me) | Me | iPr | m-F |
| 287 | L-Ala (R = Me) | Me | iPr | m-COMe |
| 288 | L-Ala (R = Me) | Me | iPr | m-Cl |
| 289 | L-Ala (R = Me) | Me | iPr | m-$CF_3$ |
| 290 | L-Ala (R = Me) | Et | iPr | m-F |
| 291 | L-Ala (R = Me) | Et | iPr | m-COMe |
| 292 | L-Ala (R = Me) | Et | iPr | m-Cl |
| 293 | L-Ala (R = Me) | Et | iPr | m-$CF_3$ |
| 294 | L-Ala (R = Me) | iPr | iPr | m-F |
| 295 | L-Ala (R = Me) | iPr | iPr | m-COMe |
| 296 | L-Ala (R = Me) | iPr | iPr | m-Cl |
| 297 | L-Ala (R = Me) | iPr | iPr | m-$CF_3$ |
| 298 | L-Ala (R = Me) | neoPent | iPr | m-F |
| 299 | L-Ala (R = Me) | neoPent | iPr | m-COMe |
| 300 | L-Ala (R = Me) | neoPent | iPr | m-Cl |
| 301 | L-Ala (R = Me) | neoPent | iPr | m-$CF_3$ |
| 302 | L-Ala (R = Me) | Bn | iPr | m-F |
| 303 | L-Ala (R = Me) | Bn | iPr | m-COMe |
| 304 | L-Ala (R = Me) | Bn | iPr | m-Cl |
| 305 | L-Ala (R = Me) | Bn | iPr | m-$CF_3$ |
| 306 | L-Ala (R = Me) | neoPent | Me | m-F |
| 307 | L-Ala (R = Me) | neoPent | Me | m-COMe |
| 308 | L-Ala (R = Me) | neoPent | Me | m-Cl |

TABLE 3-continued

| Compound No. | AA (R) | R' | R" | X |
|---|---|---|---|---|
| 309 | L-Ala (R = Me) | neoPent | Me | m-CF$_3$ |
| 310 | L-Ala (R = Me) | neoPent | Et | m-F |
| 311 | L-Ala (R = Me) | neoPent | Et | m-COMe |
| 312 | L-Ala (R = Me) | neoPent | Et | m-Cl |
| 313 | L-Ala (R = Me) | neoPent | Et | m-CF$_3$ |
| 314 | L-Ala (R = Me) | neoPent | iPr | m-F |
| 315 | L-Ala (R = Me) | neoPent | iPr | m-COMe |
| 316 | L-Ala (R = Me) | neoPent | iPr | m-Cl |
| 317 | L-Ala (R = Me) | neoPent | iPr | m-CF$_3$ |
| 318 | L-Ala (R = Me) | neoPent | neoPent | m-F |
| 319 | L-Ala (R = Me) | neoPent | neoPent | m-COMe |
| 320 | L-Ala (R = Me) | neoPent | neoPent | m-Cl |
| 321 | L-Ala (R = Me) | neoPent | neoPent | m-CF$_3$ |
| 322 | L-Ala (R = Me) | neoPent | Bn | m-F |
| 323 | L-Ala (R = Me) | neoPent | Bn | m-COMe |
| 324 | L-Ala (R = Me) | neoPent | Bn | m-Cl |
| 325 | L-Ala (R = Me) | neoPent | Bn | m-CF$_3$ |
| 326 | Gly (R = H) | Et | Et | m-F |
| 327 | Gly (R = H) | Et | Et | m-COMe |
| 328 | Gly (R = H) | Et | Et | m-Cl |
| 329 | Gly (R = H) | Et | Et | m-CF$_3$ |
| 330 | Gly (R = H) | Bn | Bn | m-F |
| 331 | Gly (R = H) | Bn | Bn | m-COMe |
| 332 | Gly (R = H) | Bn | Bn | m-Cl |
| 333 | Gly (R = H) | Bn | Bn | m-CF$_3$ |
| 334 | Gly (R = H) | Bn | Et | m-F |
| 335 | Gly (R = H) | Bn | Et | m-COMe |
| 336 | Gly (R = H) | Bn | Et | m-Cl |
| 337 | Gly (R = H) | Bn | Et | m-CF$_3$ |
| 338 | Gly (R = H) | Et | Bn | m-F |
| 339 | Gly (R = H) | Et | Bn | m-COMe |
| 340 | Gly (R = H) | Et | Bn | m-Cl |
| 341 | Gly (R = H) | Et | Bn | m-CF$_3$ |
| 342 | L-Trp (R = (1H-indol-3-yl)methyl) | Me | Me | m-F |
| 343 | L-Trp (R = (1H-indol-3-yl)methyl) | Me | Me | m-COMe |
| 344 | L-Trp (R = (LfF-indol-3-yl)methyl) | Me | Me | m-Cl |
| 345 | L-Trp (R = (1H-indol-3-yl)methyl) | Me | Me | m-CF$_3$ |
| 346 | L-Trp (R = (1H-indol-3-yl)methyl) | Et | Et | m-F |
| 347 | L-Trp (R = (1H-indol-3-yl)methyl) | Et | Et | m-COMe |
| 348 | L-Trp (R = (1H-indol-3-yl)methyl) | Et | Et | m-Cl |
| 349 | L-Trp (R = (1H-indol-3-yl)methyl) | Et | Et | m-CF$_3$ |
| 350 | L-Trp (R = (1H-indol-3-yl)methyl) | Bn | Et | m-F |
| 351 | L-Trp (R = (1H-indol-3-yl)methyl) | Bn | Et | m-COMe |
| 352 | L-Trp (R = (1H-indol-3-yl)methyl) | Bn | Et | m-Cl |
| 353 | L-Trp (R = (1H-indol-3-yl)methyl) | Bn | Et | m-CF$_3$ |
| 354 | L-Trp (R = (1H-indol-3-yl)methyl) | Et | Bn | m-F |
| 355 | L-Trp (R = (1H-indol-3-yl)methyl) | Et | Bn | m-COMe |
| 356 | L-Trp (R = (1H-indol-3-yl)methyl) | Et | Bn | m-Cl |
| 357 | L-Trp (R = (1H-indol-3-yl)methyl) | Et | Bn | m-CF$_3$ |
| 358 | L-Trp (R = (1H-indol-3-yl)methyl) | Bn | Bn | m-F |
| 359 | L-Trp (R = (1H-indol-3-yl)methyl) | Bn | Bn | m-COMe |
| 360 | L-Trp (R = (1H-indol-3-yl)methyl) | Bn | Bn | m-Cl |
| 361 | L-Trp (R = (1H-indol-3-yl)methyl) | Bn | Bn | m-CF$_3$ |
| 362 | L-Val (R = iPr) | Me | iPr | m-F |
| 363 | L-Val (R = iPr) | Me | iPr | m-COMe |
| 364 | L-Val (R = iPr) | Me | iPr | m-Cl |
| 365 | L-Val (R = iPr) | Me | iPr | m-CF$_3$ |
| 366 | L-Val (R = iPr) | Et | iPr | m-F |
| 367 | L-Val (R = iPr) | Et | iPr | m-COMe |
| 368 | L-Val (R = iPr) | Et | iPr | m-Cl |
| 369 | L-Val (R = iPr) | Et | iPr | m-CF$_3$ |
| 370 | L-Val (R = iPr) | iPr | iPr | m-F |
| 371 | L-Val (R = iPr) | iPr | iPr | m-COMe |
| 372 | L-Val (R = iPr) | iPr | iPr | m-Cl |
| 373 | L-Val (R = iPr) | iPr | iPr | m-CF$_3$ |
| 374 | L-Val (R = iPr) | neoPent | iPr | m-F |

TABLE 3-continued

| Compound No. | AA (R) | R' | R" | X |
|---|---|---|---|---|
| 375 | L-Val (R = iPr) | neoPent | iPr | m-COMe |
| 376 | L-Val (R = iPr) | neoPent | iPr | m-Cl |
| 377 | L-Val (R = iPr) | neoPent | iPr | m-CF$_3$ |
| 378 | L-Val (R = iPr) | Bn | iPr | m-F |
| 379 | L-Val (R = iPr) | Bn | iPr | m-COMe |
| 380 | L-Val (R = iPr) | Bn | iPr | m-Cl |
| 381 | L-Val (R = iPr) | Bn | iPr | m-CF$_3$ |
| 382 | L-Val (R = iPr) | neoPent | Me | m-F |
| 383 | L-Val (R = iPr) | neoPent | Me | m-COMe |
| 384 | L-Val (R = iPr) | neoPent | Me | m-Cl |
| 385 | L-Val (R = iPr) | neoPent | Me | m-CF$_3$ |
| 386 | L-Val (R = iPr) | neoPent | Et | m-F |
| 387 | L-Val (R = iPr) | neoPent | Et | m-COMe |
| 388 | L-Val (R = iPr) | neoPent | Et | m-Cl |
| 389 | L-Val (R = iPr) | neoPent | Et | m-CF$_3$ |
| 390 | L-Val (R = iPr) | neoPent | iPr | m-F |
| 391 | L-Val (R = iPr) | neoPent | iPr | m-COMe |
| 392 | L-Val (R = iPr) | neoPent | iPr | m-Cl |
| 393 | L-Val (R = iPr) | neoPent | iPr | m-CF$_3$ |
| 394 | L-Val (R = iPr) | neoPent | neoPent | m-F |
| 395 | L-Val (R = iPr) | neoPent | neoPent | m-COMe |
| 396 | L-Val (R = iPr) | neoPent | neoPent | m-Cl |
| 397 | L-Val (R = iPr) | neoPent | neoPent | m-CF$_3$ |
| 398 | L-Val (R = iPr) | neoPent | Bn | m-F |
| 399 | L-Val (R = iPr) | neoPent | Bn | m-COMe |
| 400 | L-Val (R = iPr) | neoPent | Bn | m-Cl |
| 401 | L-Val (R = iPr) | neoPent | Bn | m-CF$_3$ |
| 402 | L-Val (R = iPr) | Et | Et | m-F |
| 403 | L-Val (R = iPr) | Et | Et | m-COMe |
| 404 | L-Val (R = iPr) | Et | Et | m-Cl |
| 405 | L-Val (R = iPr) | Et | Et | m-CF$_3$ |

(wherein wherein AA represents the amino acid from which the side chain "R" is derived, Et is ethyl, Me is methyl, nBu is n-butyl, MeCyPr is methylcyclopropyl (i.e., —CH$_2$-cyclopropyl), Bn is benzyl, iPr is isopropyl, neoPent is neopentyl, L-Ala is L-alanine, Gly is glycine, L-Trp is L-tryptophan, and L-Val is L-valine).

Yet another embodiment is a compound having the formula:

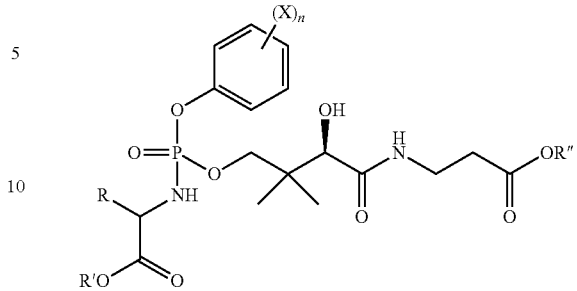

Formula F or a pharmaceutically acceptable salt thereof, wherein
R is an amino acid side chain:
each occurrence of X is, independently, halogen (e.g., Cl or F), alkyl (e.g., $C_{1-8}$ alkyl, $C_{1-6}$ alkyl, or $C_{1-4}$ alkyl), alkenyl (e.g., $C_{1-8}$ alkenyl, $C_{1-6}$ alkenyl, or $C_{1-4}$ alkenyl), halogenated alkyl (e.g., $C_1$-$C_6$ alkyl such as —CF$_3$), —CN, —NO$_2$, —C(O)$_2$R$^1$, —C(O)R$^1$, or —OR$^2$;
each occurrence of R$^1$ is, independently, $C_{1-6}$ alkyl (e.g., methyl or ethyl);
each occurrence of R$^2$ is, independently. $C_{1-6}$ alkyl (e.g., methyl or ethyl), $C_2$-$C_6$ alkenyl, $C_2$-$C_6$ alkynyl, aryl or polyethylene glycol (PEG) (e.g., where the PEG has 2 to 100 repeating units);
n is 1, 2, 3, 4 or 5 (e.g., 1 or 2);
R' is substituted or unsubstituted $C_7$-$C_{20}$ alkyl (such as unsubstituted $C_7$-$C_{20}$ alkyl) and substituted or unsubstituted $C_7$-$C_{20}$ alkenyl; and
R" is substituted or unsubstituted $C_1$-$C_{20}$ alkyl (e.g., $C_1$-$C_8$ alkyl or $C_1$-$C_6$ alkyl), substituted or unsubstituted $C_2$-$C_{20}$ alkenyl (e.g., $C_2$-$C_6$ alkenyl), substituted or unsubstituted alkynyl (e.g., $C_2$-$C_6$ alkynyl), substituted or unsubstituted cycloalkyl (e.g., $C_3$-$C_8$ cycloalkyl), substituted or unsubstituted cycloalkenyl (e.g., $C_3$-$C_8$ cycloalkenyl), substituted or unsubstituted cycloalkylalkyl (e.g., $C_3$-$C_8$ cycloalkyl($C_1$-$C_6$ alkyl)), substituted or unsubstituted cycloalkenylalkyl (e.g., $C_3$-$C_8$ cycloalkenyl($C_1$-$C_6$ alkyl)), substituted or unsubstituted aryl, substituted or unsubstituted arylalkyl, substituted or unsubstituted heterocyclyl, substituted or unsubstituted heteroaryl, substituted or unsubstituted heterocyclylalkyl, substituted or unsubstituted heteroarylalkyl or PEG (e.g., where the PEG has 2 to 100 repeating units), each of which is optionally substituted by one or more halogen (e.g., fluorine).

In one embodiments of formula F, each occurrence of X is, independently, halogen (e.g., Cl or F), alkyl (e.g., $C_{1-8}$ alkyl, $C_{1-6}$ alkyl, or $C_{1-4}$ alkyl), alkenyl (e.g., $C_{1-8}$ alkenyl, $C_{1-6}$ alkenyl, or $C_{1-4}$ alkenyl), halogenated alkyl (e.g., $C_1$-$C_6$ alkyl such as —CF$_3$), —CN, —NO$_2$, —C(O)$_2$R$^1$, —C(O) R$^1$, or —OR$^2$, wherein at least one occurrence of X is not halogen.

In another embodiment, each occurrence of X is, independently, halogen (e.g., Cl or F), halogenated alkyl (e.g., $C_1$-$C_6$ alkyl such as —CF$_3$), —CN, —NO$_2$, —C(O)$_2$R$^1$, or —C(O)R$^1$.

In one other embodiment of formula F, each occurrence of X is, independently, halogen (e.g., Cl or F), halogenated alkyl (e.g., $C_1$-$C_6$ alkyl such as —CF$_3$), —CN, —NO$_2$, —C(O)$_2$R$^1$, or —C(O)R$^1$, wherein at least one occurrence of X is not halogen.

In one embodiment of the compound of formula F, R' is $C_8$-$C_{20}$ alkyl (e.g., $C_8$-$C_{12}$ alkyl, $C_8$-$C_{10}$ alkyl, $C_{10}$-$C_{20}$ alkyl, $C_{10}$-$C_{16}$ alkyl or $C_8$-$C_{16}$ alkyl).

In one embodiment of the compound of formula F, R" is $C_1$-$C_6$ alkyl (e.g., methyl, ethyl, n-propyl, i-propyl, n-butyl, i-butyl, t-butyl, neopentyl), benzyl, cyclohexyl, or methylcyclopropyl.

In one embodiment, the amino acid side chain in the definition of R is that of an unnatural amino acid. In one preferred embodiment, the amino acid side chain in the definition of R is that of a natural amino acid (e.g., a natural L-amino acid). R may be attached to the carbon depicted such that the carbon has the R or S absolute configuration (D or L relative configuration). In a more preferred embodiment, R is the side chain of a proteinogenic amino acid. In one embodiment, the compounds of formula F have the following stereochemistry:

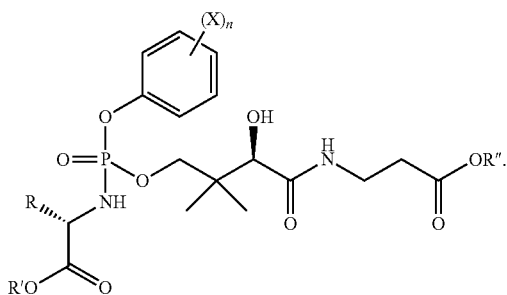

Formula F1

In one embodiment of any of the foregoing compounds, the compound of the present invention does not form an ion at physiological pH (e.g., at a pH of between about 7.3 and about 7.5, such as at a pH of between about 7.3 and about 7.4, such as at a pH of about 7.4 or at a pH of about 7.365).

In another embodiment, the compound of the present invention has a pKa value of about 7.

Pharmaceutical Compositions and Methods of Treatment

Another embodiment of the invention is a pharmaceutical composition comprising a compound of the present invention, and a pharmaceutically acceptable excipient. In one embodiment, the pharmaceutical composition includes an effective amount of the compound to treat a neurologic disorder. The pharmaceutical composition may be a dosage unit form, such as a tablet or capsule.

Yet another embodiment is a method of increasing Coenzyme A levels in a human subject (e.g., a subject having a deficiency of Coenzyme A, pantothenate kinase, and/or 4'-phosphopantothenate). The method comprises administering to the subject an effective amount of a compound of the present invention. In one embodiment, the subject has a pantothenate kinase (PANK) gene defect.

Yet another embodiment is a method of treating a disorder associated with a deficiency of pantothenate kinase, 4'-phosphopantothenate, or Coenzyme A in a subject. The method comprises administering to the subject an effective amount of a compound of the present invention.

Yet another embodiment is a method of treating pantothenate kinase-associated neurodegeneration in a subject. The method comprises administering to the subject an effective amount of a compound of the present invention. The subject may suffer from neurodegeneration with brain iron accumulation.

Yet another embodiment is a method of treating Parkinson's disease in a subject. The method comprises administering to the subject an effective amount of a compound of the present invention.

Yet another embodiment is a method of treating cells or tissue involved in a pathology characterized by abnormal neuronal function in a subject. The method comprises administering to the subject an effective amount of a compound of the present invention. The pathology may be dystonia, extrapyramidal effects, dysphagia, rigidity and/or stiffness of limbs, choreoathetosis, tremor, dementia, spasticity, muscle weakness, or seizure.

Yet another embodiment is a method of treating cells or tissues involved in a pathology characterized by dysfunctional neuronal cells caused by misregulation of the gene associated with the enzyme pantothene kinase. The method comprises administering to the subject an effective amount of a compound of the present invention.

Yet another embodiment is a method of treating a pathology characterized by dysfunctional neuronal cells caused by misregulation of the gene associated with the enzyme pantothene kinase in a subject. The method comprises administering to the subject an effective amount of a compound of the present invention.

Yet another embodiment is a method of treating cells or tissues involved in a pathology characterized by dysfunctional neuronal cells caused by misregulation of the expression of the gene associated with the enzyme pantothene kinase. The method comprises administering to the subject an effective amount of a compound of the present invention.

Yet another embodiment is a method of treating a pathology characterized by dysfunctional neuronal cells caused by misregulation of the expression of the gene associated with the enzyme pantothene kinase in a subject. The method comprises administering to the subject an effective amount of a compound of the present invention.

Yet another embodiment is a method of treating a subject having neuronal cells with an over accumulation of iron. The method comprises administering to the subject an effective amount of a compound of the present invention. Another embodiment is a method of treating a subject having neurodegeneration with brain iron accumulation by administering to the subject an effective amount of a compound of the present invention.

In the aforementioned methods, the subject may be a child (for example, 10 to 15 years old) or an adult.

Pharmaceutical Formulations and Routes of Administration

The compounds of the present invention may be administered by a variety of routes including orally and by injection (e.g. subcutaneously, intravenously, and intraperitoneally).

The compounds may be administered orally in the form of a solid or liquid dosage form. In both, the compound may be coated in a material to protect it from the action of acids and other natural conditions which may inactivate the compound. The compounds may be formulated as aqueous solutions, liquid dispersions, (ingestible) tablets, buccal tablets, troches, capsules, elixirs, suspensions, syrups, and wafers. The oral dosage forms may include excipients known in the art, such as binders, disintegrating agents, flavorants, antioxidants, and preservatives. Liquid dosage forms may include diluents such as saline or an aqueous buffer.

The compounds may also be administered by injection. Formulations suitable for injection may include sterile aqueous solutions (where water soluble) or dispersions, and sterile powders for the extemporaneous preparation of sterile injectable solutions or dispersions. The composition may be sterile and be fluid to the extent that easy syringability exists. It may be stable under the conditions of manufacture and storage and be preserved against the contaminating action of microorganisms such as bacteria and fungi. The carrier can be a solvent or dispersion medium containing, for example, water, ethanol, polyol (such as, glycerol, propylene glycol, and liquid polyethylene glycol), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, and ascorbic acid. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the methods of preparation include vacuum drying and freeze-drying which yields a powder of the active ingredient (i.e., the therapeutic compound) plus any additional desired ingredient from a previously sterile-filtered solution thereof.

The actual dosage amount of the compound administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject.

In one embodiment, a human subject is administered the daily doses of from about 0.01 mg/kg to about 100 mg/kg.

Single or multiple doses of the compounds are contemplated. Desired time intervals for delivery of multiple doses can be determined by one of ordinary skill in the art employing no more than routine experimentation. As an example, subjects may be administered two doses daily at approximately 12 hour intervals. In some embodiments, the compound is administered once a day.

The compounds may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months. In other embodiments, the invention provides that the agent(s) may taken orally and that the timing of which is or is not dependent upon food intake. Thus, for example, the agent can be taken every morning and/or every evening, regardless of when the subject has eaten or will eat.

Combination Therapy

In addition to being used as a monotherapy, the compounds may also find use in combination therapies. Effective combination therapy may be achieved with a single composition or pharmacological formulation that includes both agents, or with two distinct compositions or formulations, administered at the same time, wherein one composition includes a compound of this invention, and the other includes the second agent(s). Alternatively, the therapy may precede or follow the other agent treatment by intervals ranging from minutes to months.

The additional agent or agents may be selected from any agent or agents useful for treating a neurological disorder, for example any agent or agents useful for treating a deficiency of pantothenate kinase, 4'-phosphopantothenate, or Coenzyme A. In one embodiment, the additional agent or agent is useful in improving cognitive function, e.g., an acetylcholinesterase inhibitor, such as physostigmine, neostigmine, pyridostigmine, ambenonium, demarcarium, rivastigmine, galantamine, donezepil, and combinations thereof. In another embodiment, the additional agent or agents is an iron chelator, such as deferiprone, deferoxamine, deferasirox, and combinations thereof.

Synthesis of Phosphopantothenate Derivatives

Yet another embodiment of the invention is a method of preparing a compound of formula A, A1, A2, B, C, D, E, E1, E2, E3, E4, E5, F, or F1 by:

(a) protecting both hydroxyl groups of pantothenic acid;

(b) esterifying the acid moiety of the protected pantothenic acid to form a compound of the formula:

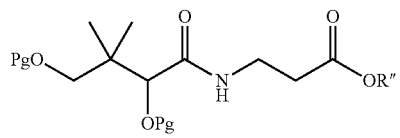

where each Pg independently represent a protecting group, and R" is defined as above;

(c) deprotecting the hydroxyl groups:

(d) phosphorylating the deprotected compound with a compound of the formula:

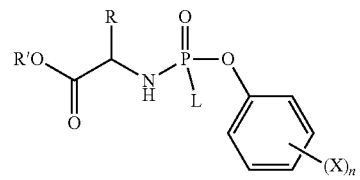

wherein (i) L is a leaving group (e.g., halogen such as chloro), (ii)R, R', and X are defined as above with respect to formula A, A1, A2, B, C, D, E, E1, E2, E3, E4, E5, F, or F1, and (iii) n is 0, 1, 2, 3, 4, or 5; and (e) optionally, forming a salt of the compound formed in step (d).

Yet another embodiment is a method of preparing a compound of formula A, A1, A2, B, C, D, E, E1, E2, E3, E4, E5, F, or F1 by:

(a) esterifying pantothenic acid with an alcohol of the formula R"OH to form a compound of the formula:

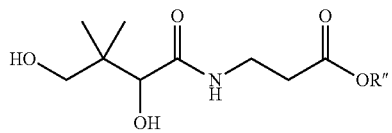

wherein R″ is defined as above:

(b) phosphorylating the esterified compound with a compound of the formula:

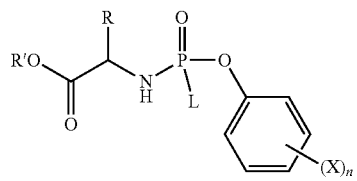

wherein (i) L is a leaving group (e.g., halogen), (ii) R, R′, X and n are defined as above with respect to formula A, A1, A2, B, C, D, E, E1, E2, E3, E4, E5, F, or F1, and (iii) n is 0, 1, 2, 3, 4, or 5; and (c) optionally, forming a salt of the compound formed in step (b). The esterification in step (a) can be performed by subjecting pantothenic acid to Fischer esterification conditions.

The compounds of the present invention can be prepared from pantothenic acid (vitamin B5), which is readily available. The synthesis of pantothenic acid is described, for example, in U.S. Pat. Nos. 2,676,976 and 2,870,188, which are herein incorporated by reference in their entirety.

The compound of formula A, A1, A2, B, C, D, E, E1, E2, E3, E4, E5, F, or F1 can be prepared by (a) protecting both hydroxyl groups of pantothenic acid, (b) esterifying the acid moiety of the protected pantothenic acid to form a compound of the formula:

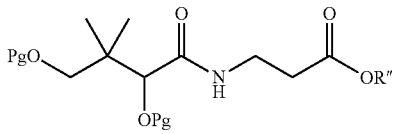

where each Pg independently represent a protecting group, and R″ is defined as above, (c) deprotecting the hydroxyl groups, (d) phosphorylating the deprotected compound with a compound of the formula:

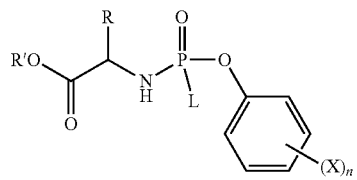

wherein (i) L is a leaving group (e.g., halogen), and (ii) R, R′, and X are defined as above with respect to formula A, A1, A2, B, C, D, E, E1, E2, E3, E4, E5, F, or F1, and (iii) n is 0, 1, 2, 3, 4, or 5; and (e) optionally, forming a salt of the compound formed in step (d). This reaction scheme is shown below (where L is Cl):

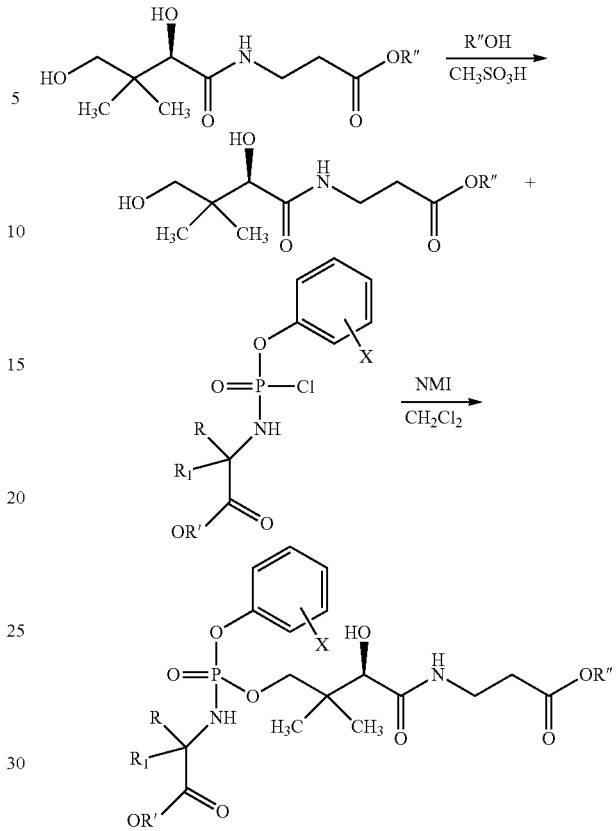

(Note: R¹ in the last step can be hydrogen.)

Protection and deprotection can be performed by any method known in the art, such as those described in T. W. Green and P. G. M. Wuts, *Protective Groups in Organic Synthesis*, Wiley-Interscience, New York, 1999.

Formation of an ester (R″) may be accomplished by, for example, reacting diprotected pantothenic acid with an appropriate alcohol, treatment with an acid in the presence of an excess of alcohol, and dicyclohexyldicarbodimide (DCC), or diethylazodicarboxylate (DEAD) and triphenylphosphine (a Mitsunobu reaction). Alternatively, the protected pantothenic acid can be converted to the corresponding acid chloride (for example, with thionyl chloride or oxalyl chloride), followed by treatment with the corresponding alcohol.

As an alternative to steps (a) to (c), pantothenic acid can be esterified with an alcohol of the formula R″OH, for example, by subjecting pantothenic acid to Fischer esterification conditions (i.e., excess alcohol, and catalytic acid under reflux).

The primary hydroxyl group on the compound formed in step (c) can be selectively phosphorylated. See J. D. Patrone, J. Yao, N. E. Scott, and G. D. Dotson, "Selective Inhibitors of Bacterial Phosphopantothenoylcysteine Synthetase", *J. Am. Chem. Soc.*, 2009, 131, 16340-16341). The conditions described in D. M. Lehsten, D. N. Baehr, T. J. Lobl, and A. R. Vaino, "An Improved Procedure for the Synthesis of Nucleoside Phosphoramidates", *Organic Process Research & Development*, 2002, 6, 819-822, can be used for this reaction. This reference is herein incorporated by reference in its entirety.

Optionally, an optically pure product can be obtained by performing a chiral separation of the final product, or one of the intermediates between steps in the synthesis.

Alternatively, the compounds of the present invention can be prepared by modifying the route described in B. S. Ross et al., "Synthesis of Diastereomerically Pure Nucleotide Phosphoramidates", *J. Org. Chem.*, 2011, 76, 8311-8319. This route can produce an optically pure product without performing a final chiral separation step.

EXAMPLES

Example 1

Ethyl 3-((2R)-4-(((((S)-1-ethoxy-1-oxopropan-2-yl)amino)(3-fluorophenoxy) phosphoryl)oxy)-2-hydroxy-3,3-dimethylbutanamido)propanoate (Table 3, Compound No. 258)

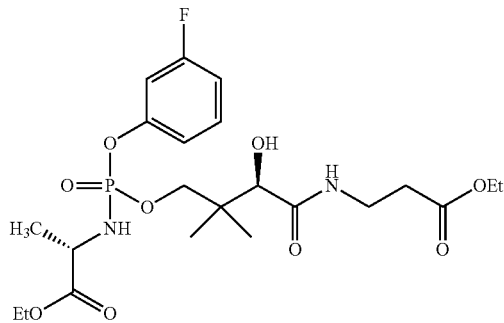 [SMILES: CCOC(=O)CCNC(=O)[C@H](O)C(C)(C)COP(=O)(N[C@@H](C)C(=O)OCC)Oc1cccc(F)c1]

L-Alanine ethyl ester hydrochloride is suspended in $CH_2Cl_2$ and treated with 3-fluorophenyl phosphorodichloridate at $-10°$ C. and under an atmosphere of nitrogen. The well-stirred mixture is then treated dropwise with N-methylimidazole. After 1 hr. and still at $-10°$ C., ethyl pantothenate in $CH_2Cl_2$ is added slowly. This mixture is allowed to warm to room temperature, and after 3 hrs, methanol is added. Extraction is performed sequentially with 1 M HCl, water, 5% $NaHCO_3$, and brine. The organic phase is dried ($Na_2SO_4$), and the solvent is evaporated. This material may be purified by flash column chromatography using 30 g of silica gel and eluting with 1:1 EtOAc/hexanes containing 5% EtOH.

Example 2

Methyl 3-((2R)-4-(((4-cyanophenoxy)((S)-1-methoxy-1-oxopropan-2-yl)amino)phosphoryl)oxy)-2-hydroxy-3,3-dimethylbutanamido)propanoate (Table 2, Compound No. 38)

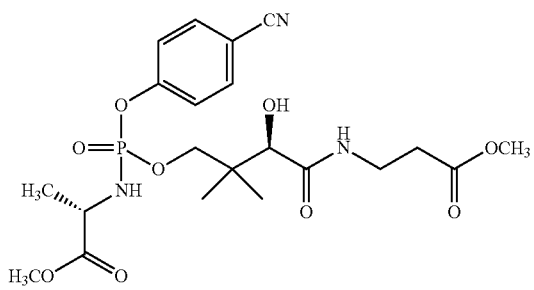 [SMILES: COC(=O)CCNC(=O)[C@H](O)C(C)(C)COP(=O)(N[C@@H](C)C(=O)OC)Oc1ccc(C#N)cc1]

L-alanine methyl ester hydrochloride is suspended in dichloromethane and treated with 4-cyanophenyl phosphodichloridate at $-78°$ C. under an atmosphere of argon. Diisopropylethylamine is added dropwise. The mixture is stirred at $-78°$ C. for 30 minutes, then allowed to warm to room temperature for 1 hr. The mixture is chilled to $-5°$ C. and methyl pantothenate added dropwise in dichloromethane. N-methylimidazole is then added, and after stirring at $-5°$ C. for 30 mins and room temperature for 1 hour, methanol is added. The mixture is washed sequentially with water (30 mL), 5% citric acid (30 mL), and brine (10 mL). The organic phase is dried ($Na_2SO_4$) and the solvent is removed under reduced pressure. Purification may be achieved with a 1:1 mixture of EtOAc:hexane.

Example 3

In Vitro Bacterial Testing

SJ16 is a strain of *Escherichia coli* that requires addition of pantothenic acid to proliferate (i.e., it has a mutation such that pantothenic acid is inactive). Thus, it serves as a useful assay in determining whether a compound can rescue an organism deficient in PANK, the cause of PKAN. Compounds of the present invention may be tested for toxicity and for the ability to support growth of *Escherichia coli* K-12 strains SJ16 (see. e.g., Jackowski et al., *J. Bacteriol.*, 148, 926-932, 1981) and DV70 (see. e.g., Vallari et al., *J. Bacteriol.*, 169, 5795-5800, 1987) under permissive and non-permissive conditions. The test compound in a solvent (dimethylsulfoxide, DMSO) is added to growth medium at a final concentration of 8 μM. Solvent alone (DMSO) is added to the growth medium at a final concentration ≤0.1% as a control.

Strain SJ16 is grown at 37° C. for 18 hours on a solid medium containing agar (1.5%). M9 minimal essential salts (see, Miller, Experiments in Molecular Genetics. Cold Spring Harbor Laboratory, Cold Spring Harbor, N.Y., 1972), glucose (0.4%), methionine (50 μg/ml), and with (permissive) or without (non-permissive) calcium pantothenate (1 μM). Lack of growth with calcium pantothenate supplementation indicates toxicity. Growth without calcium pantothenate supplementation indicates the ability of the bacteria to metabolize the compound to yield pantothenate or β-alanine.

Strain DV70 is grown at 30° C. (permissive) or 42° C. (non-permissive) for 18 hours on solid medium containing agar (1.5%), M9 minimal essential salts, glucose (0.4%), methionine (50 μg/ml), and calcium pantothenate (1 μM). Lack of growth at 30° C. indicates toxicity. Growth at 42° C. indicates metabolism of the compound and subsequent conversion to coenzyme A by the bacteria.

Example 4

The compounds described herein may be tested in immortalized human cells (HEK 293T). The amount of acetyl-CoA (the downstream result of PANK) following administration of the compounds is measured by mass spectrometry.

Example 5

In Vivo Testing

Compounds of the invention were tested for efficacy in Pank1$^{-/-}$ mice (strain 129SvJ×C57BL/6J background), which were compared with age-matched Pank1$^{+/+}$ (strain 129SvJ×C57BL/6J) littermates, ages 8-12 weeks. Each mouse was identified with a coded ear tag and weighed on the first day of testing. Each compound was administered to 4-5 mice by intraperitoneal injection at a dose of 1.2 µmoles/g body weight in 5 µL dimethylsulfoxide once daily for 5 days, and mice were then fasted overnight, weighed, and euthanized. Untreated mice received 5 µL dimethylsulfoxide once daily for 5 days and then were fasted overnight prior to weighing and euthanasia. Livers were excised from each mouse, aliquots were snap-frozen in liquid nitrogen, and stored at −80° C. Within 7 days, liver samples were thawed on ice, weighed, and analyzed for Coenzyme A content as described below. Efficacy was indicated by a statistically significant increase in the liver Coenzyme A levels in the Pank1$^{-/-}$ mice as compared to the liver from untreated Pank1$^{-/-}$ mice and by equivalence in comparison with Coenzyme A levels in untreated Pank1$^{+/+}$ mice.

CoA Measurements: Extraction of Fibroblasts and Liver and Derivatization of Coenzyme A Prior to High Pressure Liquid Chromatography (HPLC)

Extraction of fibroblasts or liver were performed by modification of a method described previously (see, Minkler et al., *Anal. Biochem.*, 376, 275-276, 2008). Coenzyme A derivatization were performed by modification of a method described previously (see. Shimada et al., *J. Chromatogr. B Biomed. Appl.*, 659, 227-241, 1994).

Liver (20-50 mg) was homogenized in 2 mL of 1 mM KOH, and the pH was adjusted to 12 with 0.25 M KOH. Fibroblasts were scraped off the culture dish and collected in 1 mL of water, which was transferred to 200 µL of 0.25 M NaOH. The liver homogenate was then incubated at 55° C. for 2 hours and the fibroblast cells were incubated for 1 hour at 55° C. The pH was adjusted to pH 8 with 1 M Trizma-HCl, and 10 µL of 100 mM monobromobimane (mBBr, Life Technologies, NY) was added for 2 hours in the dark. The reaction was acidified with acetic acid, and centrifuged at 500 g for 15 minutes. The supernatant was then added to a 2-(2-pyridyl)ethyl column (Supelco), which was equilibrated with 1 mL of 50% methanol/2% acetic acid. The column was washed with 2×1 mL 50% methanol/2% acetic acid and 1 mL water. Samples are eluted with 2×1 mL 50 mM ammonium formate in 95% ethanol. Samples were evaporated under nitrogen and resuspended in 300 µL of water. Samples were spun through a Spin-X Centrifuge Tube Filter (0.22 µm Cellulose Acetate, Costar) to remove any precipitants before HPLC.

Coenzyme A Quantification by HPLC

The mBBr derivative of Coenzyme A was separated by reverse-phase HPLC using a Gemini $C_{18}$ 3 µm column (150×4.60 mm) from Phenomenex (Torrance, Calif.). The chromatography system used was a Waters e2695 separation module with a UV/Vis detector and controlled by the Empower 3 software. Solvent A was 50 mM potassium phosphate pH 4.6, and solvent B was 100% acetonitrile. 20 µL of sample was injected onto the column, and the flow rate was 0.5 mL/min. The HPLC program is the following: starting solvent mixture of 90% A/10% B, 0 to 2 min isocratic with 10% B, 2 to 9 min linear gradient from 10% B to 25% B, 9 to 23 min concave gradient from 25% B to 40% B, 23 to 25 min linear gradient from 40% to 10%, and 25 to 30 min isocratic with 10% B. The detector was set at λ393 nm. The area under the mBBr derivatized Coenzyme A peak was integrated and was compared to a standard concentration curve of mBBr-Coenzyme A prepared from commercial Coenzyme A.

Levels of Coenzyme A (CoA) in treated Pank1$^{-/-}$ mice as a percentage of CoA levels in untreated Pank1$^{-/-}$ mice are shown in Table 4 below.

TABLE 4

| Compound No. | AA (R) | R' | R" | X | CoA (% KO) |
|---|---|---|---|---|---|
| 22 | L-Ala (R = Me) | Me | Bn | N/A | 400 |
| 27 | L-Phe (R = Me) | Bn | Me | N/A | 1837 |
| 48 | L-Ala (R = Me) | Me | Me | p-F | 126 |
| 36 | L-Ala (R = Me) | Et | Et | p-F | 211 |
| 54 | L-Ala (R = Me) | Bn | Et | p-F | 1368 |
| 60 | L-Ala (R = Me) | Et | Bn | p-F | 126 |
| 66 | L-Ala (R = Me) | Bn | Bn | p-F | 653 |
| 253 | L-Ala (R = Me) | Bn | Bn | p-OMe | 675 |
| 254 | L-Ala (R = Me) | Bn | Et | p-OMe | 2200 |
| 255 | L-Ala (R = Me) | Me | Me | p-OMe | 200 |
| 256 | L-Ala (R = Me) | Et | Et | p-OMe | 237.5 |
| 257 | L-Ala (R = Me) | Et | Bn | p-OMe | 200 |

(wherein wherein AA represents the amino acid from which the side chain "R" is derived, Et is ethyl, Me is methyl, nBu is n-butyl, MeCyPr is methylcyclopropyl (i.e., —CH$_2$-cyclopropyl), Bn is benzyl, iPr is isopropyl, neoPent is neopentyl, L-Ala is L-alanine. Gly is glycine. L-Trp is L-tryptophan, and L-Val is L-valine). N/A=not applicable.

Example 6

Benzyl 3-((2R)-2-hydroxy-4-(((((S)-1-methoxy-1-oxopropan-2-yl)amino)(phenoxy)phosphoryl)oxy)-3,3-dimethylbutanamido)propanoate (Table 1, Compound No. 22)

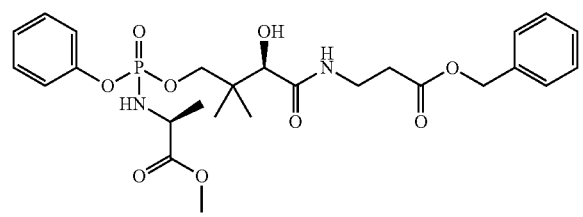 [SMILES: COC(=O)[C@H](C)NP(=O)(OCC(C)(C)[C@@H](O)C(=O)NCCC(=O)OCc1ccccc1)Oc1ccccc1]

A suspension of methyl L-alaninate hydrochloride (1 eq) in dry DCM (0.34 M) was treated at −70° C. with dichlorophosphoryloxybenzene (1 eq). A solution (4.4 M) of Et$_3$N (2.0 eq) in dry DCM was added and the resulting white suspension was stirred for 30 min at −70° C. before being warmed to room temperature. After stirring for 30 min, the mixture was cooled to −10° C. and a solution (2.5 M) of (R)-benzyl 3-(2,4-dihydroxy-3,3-dimethylbutanamido)propanoate (1.1 eq) in DCM was added dropwise. A solution (4.4 M) of freshly distilled NMI (2.0 eq) was then added and the resulting mixture was left to stir for 0.5 h at −10° C. then warmed to room temperature and stirred for a further 1 h. The reaction was quenched by addition of MeOH and then diluted with DCM. The organic phase was washed sequentially with water, 5% citric acid and brine then was dried over Na$_2$SO$_4$. The filtered organic phase was concentrated in vacuo to obtain residue that was purified by flash chromatography on SiO2 using DCM/EtOAC to furnish a mixture (30:70*) of diastereoisomers of the title compound as a colorless oil (20%). $^1$H-NMR (400 MHz, CDCl$_3$, 300K) δ 7.40-7.72 (m, 7H), 7.23-7.16 (m, 4H), 5.15 and 5.14* (s, 2H), 4.22-4.03 (m, 2H), 3.96 and 3.80* (s, 1H), 3.75 (s, 3H), 3.72-3.61 (m, 1H), 3.60-3.50 (m, 2H), 2.62-2.59 (m, 2H), 1.43-1.40 (m, 3H), 1.09 (s, 3H), 0.81 (s, 3H); $^{31}$P-NMR (400 MHz, CDCl$_3$, 300K) δ 5.93* and 5.43.

Example 7

Methyl (2S)-2-[[[(3R)-3-hydroxy-4-[(3-methoxy-3-oxopropyl)amino]-2,2-dimethyl-4-oxobutoxy]-phenoxyphosphoryl]amino]-3-methylbutanoate (Table 1, Compound No. 21)

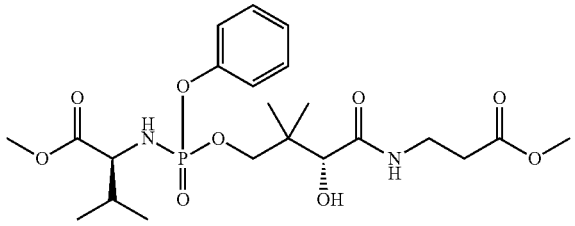

The compound was prepared following the same experimental procedure as described in Example 6.

Yield: 2% $^1$H-NMR (400 MHz, CDCl$_3$, 300K) δ 7.35-7.31 (m, 3H), 7.19-7.17 (m, 2H), 4.14-4.12 (m, 1H), 3.83-3.77 (m, 1H), 3.74 (s, 1H), 3.70 (s, 3H), 3.67 (s, 3H), 3.60-3.51 (m, 3H), 2.55-2.53 (m, 2H), 2.10-2.02 (m, 2H), 1.07 (s, 3H), 0.96-0.94 (d, 3H, J=9.89 Hz), 0.91-0.89 (d, 3H, J=6.89 Hz), 0.80 (s, 3H); $^{31}$P-NMR (400 MHz, CDCl$_3$, 300K) δ 7.08.

Example 8

Benzyl (((R)-3-hydroxy-4-((3-methoxy-3-oxopropyl)amino)-2,2-dimethyl-4-oxobutoxy)(phenoxy)phosphoryl)-L-alaninate (Table 1, Compound 24)

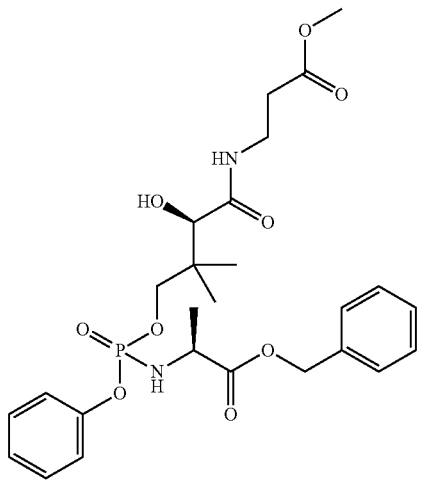 [SMILES: COC(=O)CCNC(=O)[C@H](O)C(C)(C)COP(=O)(N[C@@H](C)C(=O)OCc1ccccc1)Oc1ccccc1]

The compound was prepared following the same experimental procedure as described in Example 6.

Yield: 63.8% Diasteroisomeric ratio 54:46 $^1$H-NMR (400 MHz, CDCl$_3$, 300K) δ 7.35-7.29 (m, 6H), 7.19-7.14 (m, 4H), 5.16* and 5.15 (s, 2H), 4.18-4.12 (m, 2H), 3.94* and 3.79 (s, 1H), 3.68* and 3.67 (s, 3H), 3.72-3.61 (m, 1H), 3.59-3.50 (m, 2H), 2.60-2.49 (m, 2H), 1.45-1.40 (m, 3H), 1.08 and 1.07* (s, 3H), 0.81* and 0.79 (s, 3H); $^{31}$P-NMR (400 MHz, CDCl$_3$, 300K) δ 5.93 and 5.41*; UPLC tR 1.77 min and 1.80* min; MS (ES+) m/z 551 (M+H)$^+$.

Example 9

Benzyl (((R)-3-hydroxy-4-((3-methoxy-3-oxopropyl)amino)-2,2-dimethyl-4-oxobutoxy)(phenoxy)phosphoryl)-L-phenylalaninate (Table 1, Compound 27)

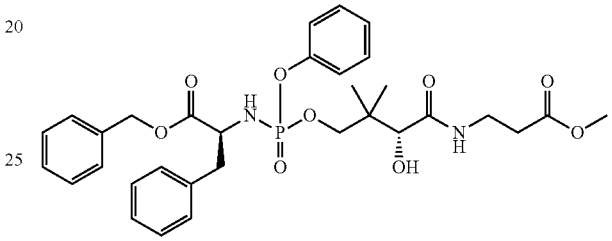

The compound was prepared following the same experimental procedure as described in Example 6.

Yield: 34% Diasteroisomeric ratio 52:48 $^1$H-NMR (400 MHz, CDCl$_3$, 300K) δ 7.34-7.00 (m, 32H), 5.11 (s, 2H), 5.10 (s, 2H), 4.32-4.21 (m, 2H), 4.03-4.17 (m, 1H), 3.83-3.88 (m, 2H), 3.67 (s, 3H), 3.66 (s, 3H), 3.59-3.48 (m, 8H), 2.99-2.90 (m, 5H), 2.50-2.56 (m, 4H), 1.03 (s, 3H), 0.98 (s, 3H), 0.78 (s, 3H), 0.64 (s, 3H); $^{31}$P-NMR (400 MHz, CDCl$_3$, 300K) δ 6.11 and 5.40*.

Example 10

Neuroblastoma Cell Assay

The compounds described herein may be tested in PANK2 silenced cells (IMR32 Human Neuroblastoma Cells). The amount of CoASH following administration of the compounds is measured by LC-MS/MS.

Cell Culture

Human neuroblastoma IMR32 cells (ATCC) were cultured in MEM (Invitrogen) supplemented with 10% fetal bovine serum, 2 mM glutamine, 1% penicillin-streptomycin, 1 mM sodium pyruvate, 1 mM non essential aminoacids and 1.5 g/l sodium bicarbonate.

Human Emryonic Kidney HEK-293T cells (ATCC) were cultured in DMEM supplemented with 10% fetal bovine serum, 1 mM glutamine, 1% penicillin-streptomycin.

The cells were maintained at 37° C. under 5% CO$_2$.

Establishment of a PANK2−/− Cell Model

For lentiviral shRNA expression, Human Emryonic Kidney HEK-293T cells (ATCC) were transfected with the appropriate pGFP-Lenti-shRNA constructs and packaging plasmids according to manufacturer's protocol (Origene Technologies, Inc.). 4 different gene-specific shRNA expression vectors designed against multiple splice variants of PANK2 (Gene ID 80025) were used for transfection. A non-silencing shRNA construct (scrambled shRNA) and an empty vector expressing GFP alone were used as negative controls. The GFP tag subcloned into the lentiviral vectors was used to monitor the transfection efficiency.

IMR32 cells were plated on 150 cm dishes 48 hrs before transduction with lentiviral particles.

Three days after transduction medium was removed and replaced with fresh medium containing 1 µg/µl puromycin. Medium was replaced every 48 hrs. Levels of PANK2 expression on selected clones was assessed by Western Blot analysis.

Cell-Based Assay on PANK2−/− Cells

Cells were plated on 6-well culture plates. After 72 hours, compounds were diluted in DMSO and added to the culture medium such that the final solvent concentration was 0.1% (v/v). Stock and working solutions of vehicle and compounds were prepared freshly prior to cell treatment. Cells were treated with 50 µM of compounds and incubated at 37° C. for 24 hours. Treatment was repeated after 24 hours with newly dissolved compound and cells were further incubated at 37° C. for additional 24 hours. Before analysis of Coenzyme A levels, cells were harvested, counted and collected in a 15 ml falcon tube and centrifuged at 200×g for 5 min at 4° C. Supernatant was removed and cell pellet was washed in 10 ml of ice-cold PBS. After centrifugation and supernatant removal, cell pellet was rapidly frozen in Liquid Nitrogen and stored at −80° C. until analysis.

LC-MS/MS Method for CoASH Determination in Neuroblastoma Cells

Cellular pellet was extracted with water 20% trifluoroacetic acid, supernatant was dried under nitrogen and reconstituted with water 0.1% formic acid containing labetatol as internal standard. LC-MS/MS was performed using an Agilent HPLC (1100 Series, USA). The LC system was interfaced with an API-4000 Q-Trap triple quadrupole mass spectrometer (AB Sciex, Toronto, Canada) equipped with a TurboIonSpray ionization source operating in positive ion mode. Analyst™ software version 1.6 (AB Sciex, Toronto, Canada) was used for data acquisition and processing. CoASH was separated using a Luna C18 column (4.6×50 mm; 5 µm particle size, Waters), column at room temperature and flow rate of 0.8 ml/min. Injection volume was 20 µl. The mobile phases consisted of water 10 mM ammonium acetate pH 7 (mobile phase A) and acetonitrile:isopropanol 90:10 (mobile phase B). Elution was performed using a gradient starting at 2% B, holding at 2% B until 0.25 min, increasing to 98% B at 2.5 min, holding at 98% B until 3.0 min, returning to 2% B at 3.5 min and holding at 2% B until 6.1 min. Precursor ions and MRM transitions used were: CoASH m/z 768.3→261.6 and 768.3→428.6.

Results for selected compounds tested in PANK2 silenced cells are reported in the following table (Table 5). Results are expressed as fold increase in CoA levels (LCMS quantification of free CoASH as described in above).

TABLE 5

| Compound No. | AA (R) | R' | R" | CoA levels (fold over vehicle treated PANK2−/− cells) |
|---|---|---|---|---|
| 3 | L-Ala (R = Me) | iPr | iPr | 1.3 |
| 4 | L-Ala (R = Me) | neoPent | iPr | 0.9 |
| 6 | L-Ala (R = Me) | neoPent | Me | 1.4 |
| 7 | L-Ala (R = Me) | neoPent | Et | 1.7 |

TABLE 5-continued

| Compound No. | AA (R) | R' | R" | CoA levels (fold over vehicle treated PANK2−/− cells) |
|---|---|---|---|---|
| 9 | L-Ala (R = Me) | neoPent | neoPent | 0.8 |
| 10 | L-Ala (R = Me) | neoPent | Bn | 0.7 |
| 22 | L-Ala (R = Me) | Me | Bn | 1.1 |
| 23 | L-Ala (R = Me) | iPr | neoPent | 0.8 |
| 24 | L-Ala (R = Me) | Bn | Me | 1.7 |
| 27 | L-Phe (R = Bn) | Bn | Me | 1.3 |

U.S. provisional patent application Ser. No. 61/895,498 filed Oct. 25, 2013, is incorporated herein by reference, in its entirety.

All publications, patents, and patent applications cited herein are hereby incorporated by reference.

What is claimed is:

1. A compound having the formula E4:

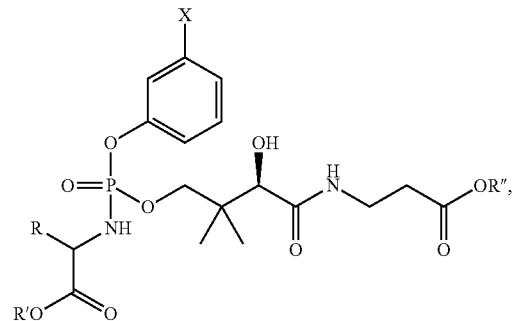

Formula E4 or a pharmaceutically acceptable salt thereof, wherein
R is methyl;
X is halogen;
R' is methyl, ethyl, or benzyl; and
R" is methyl, ethyl, or benzyl.

2. The compound of claim 1, wherein the compound has the formula E5:

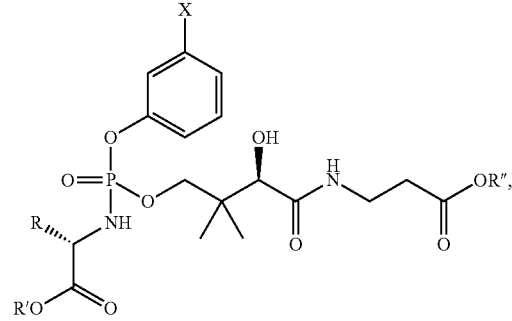

Formula E5 or a pharmaceutically acceptable salt thereof.

3. A pharmaceutical composition comprising a compound of claim 1, and a pharmaceutically acceptable excipient.

4. The pharmaceutical composition of claim 3, wherein the pharmaceutical composition is a dosage unit form.

5. The compound of claim 1, wherein R' is methyl.

6. The compound of claim 1, wherein R' is ethyl.

7. The compound of claim 1, wherein R" is methyl.

8. The compound of claim 1, wherein R" is ethyl.

9. The compound of claim 1, wherein X is Cl.

10. The compound of claim 1, wherein X is F.

11. The compound of claim 1, wherein
X is Cl;
R' is methyl; and
R" is methyl.

12. The compound of claim 1, wherein
X is Cl;
R' is ethyl; and
R" is ethyl.

13. The compound of claim 1, wherein
X is F;
R' is methyl; and
R" is methyl.

14. The compound of claim 1, wherein
X is F;
R' is ethyl; and
R" is ethyl.

\* \* \* \* \*